US011590217B2

(12) United States Patent
Rabizadeh et al.

(10) Patent No.: US 11,590,217 B2
(45) Date of Patent: *Feb. 28, 2023

(54) NEOEPITOPE VACCINE AND IMMUNE STIMULANT COMBINATIONS AND METHODS

(71) Applicant: NantCell, Inc., Culver City, CA (US)

(72) Inventors: Shahrooz Rabizadeh, Culver City, CA (US); Patrick Soon-Shiong, Culver City, CA (US)

(73) Assignee: NantCell, Inc., Culver City, CA (US)

( * ) Notice: Subject to any disclaimer, the term of this patent is extended or adjusted under 35 U.S.C. 154(b) by 326 days.

This patent is subject to a terminal disclaimer.

(21) Appl. No.: 16/390,946

(22) Filed: Apr. 22, 2019

(65) Prior Publication Data

US 2020/0016254 A1 Jan. 16, 2020

Related U.S. Application Data

(60) Provisional application No. 62/661,298, filed on Apr. 23, 2018.

(51) Int. Cl.
| | |
|---|---|
| *A61K 38/20* | (2006.01) |
| *A61K 39/395* | (2006.01) |
| *A61P 35/00* | (2006.01) |
| *C07K 14/54* | (2006.01) |
| *A61K 39/00* | (2006.01) |
| *C07K 14/715* | (2006.01) |
| *C07K 16/28* | (2006.01) |

(52) U.S. Cl.
CPC .. *A61K 39/001119* (2018.08); *C07K 14/7155* (2013.01); *C07K 16/2818* (2013.01); *C07K 16/2827* (2013.01); *A61K 2039/5154* (2013.01); *A61K 2039/5256* (2013.01); *A61K 2039/545* (2013.01); *C12N 2710/10343* (2013.01)

(58) Field of Classification Search
CPC .................. A61K 2039/5154; A61K 2039/545
USPC ............................................ 424/133.1, 277.1
See application file for complete search history.

(56) References Cited

U.S. PATENT DOCUMENTS

| | | | | |
|---|---|---|---|---|
| 11,207,392 | B2 * | 12/2021 | Soon-Shiong | ....... A61K 31/282 |
| 11,229,668 | B2 * | 1/2022 | Rabizadeh | .............. A61P 35/00 |
| 2012/0059670 | A1 | 3/2012 | Sanborn et al. | |
| 2012/0066001 | A1 | 3/2012 | Sanborn et al. | |
| 2016/0030536 | A1 | 2/2016 | Weiner et al. | |
| 2016/0339090 | A1 | 11/2016 | Hacohen et al. | |
| 2017/0196956 | A1 | 7/2017 | Nishimura et al. | |
| 2017/0266270 | A1 | 9/2017 | Foy et al. | |
| 2017/0281743 | A1 | 10/2017 | Har-Noy | |
| 2017/0312351 | A1 * | 11/2017 | Niazi | ....................... C07K 7/06 |
| 2019/0125852 | A1 * | 5/2019 | Jones | ............. A61K 39/001194 |
| 2019/0134174 | A1 * | 5/2019 | Jones | ....................... A61P 35/04 |
| 2019/0237196 | A1 * | 8/2019 | Nguyen | ............... C12Q 1/6869 |
| 2019/0285615 | A1 * | 9/2019 | Rabizadeh | ........... A61K 39/395 |
| 2019/0381156 | A1 * | 12/2019 | Soon-Shiong | .......... A61P 37/04 |
| 2020/0046817 | A1 * | 2/2020 | Rabizadeh | ......... A61K 39/3955 |
| 2020/0282032 | A1 * | 9/2020 | Jones | ............. A61K 39/001176 |
| 2020/0297830 | A1 * | 9/2020 | Niazi | ...................... A61P 43/00 |
| 2021/0046177 | A1 * | 2/2021 | Rice | ....................... C12N 15/86 |
| 2021/0113672 | A1 * | 4/2021 | Niazi | ...................... A61P 35/00 |
| 2021/0138056 | A1 * | 5/2021 | Jones | ............. A61K 39/001194 |
| 2021/0188933 | A1 * | 6/2021 | Lee | ...................... C12N 5/0634 |

FOREIGN PATENT DOCUMENTS

| | | |
|---|---|---|
| TW | 201803598 A | 2/2018 |
| WO | 2011/139345 A2 | 11/2011 |
| WO | 2013/062505 A1 | 5/2013 |
| WO | 2014/059036 A1 | 4/2014 |
| WO | 2014/193982 A1 | 12/2014 |
| WO | 2014/210611 A1 | 12/2014 |
| WO | 2015/069770 A1 | 5/2015 |
| WO | 2015/184439 A1 | 12/2015 |
| WO | 2016/004060 A2 | 1/2016 |
| WO | 2016/118527 A1 | 7/2016 |
| WO | 2016/172249 A1 | 10/2016 |
| WO | 2017/035392 A1 | 3/2017 |
| WO | 2017/066256 A2 | 4/2017 |
| WO | 2017/118695 A1 | 7/2017 |
| WO | 2017/143449 A1 | 8/2017 |
| WO | 2017/156349 A1 | 9/2017 |
| WO | 2017/205810 A1 | 11/2017 |
| WO | 2017/210579 A1 | 12/2017 |
| WO | 2018/005973 A1 | 1/2018 |
| WO | 2020/096640 A2 | 5/2020 |

OTHER PUBLICATIONS

Berraondo et al (British Journal of Cancer vol. 120, pp. 6-15 (2019).*
Liu (Yale J Biol Med. Dec. 2014; 87(4): 481-489).*
Conlon et al. (Journal of Interferon & Cytokine Research vol. 39(1):6-21 (2019)).*
Barrueto et al. (Translational Oncology 13(3):1-10 (Mar. 2020)).*
Marin-Acevedo et al. (Journal of Hematology & Oncology (2018) 11:39).*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3)793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Huang et al. (Appl Microbiol Biotechnol (2010) 87:401—410).*
De Corte et al. (Institute of Professional Representatives before the European Patent Office/European Patent Institute/epi ; 1 (19): (2019.*
Vajda et al., Current Opinion in Structural Biology, 67 pp. 226-231 (2021).*

(Continued)

*Primary Examiner* — Lynn A Bristol
(74) *Attorney, Agent, or Firm* — Martin Fessenmaier; Umberg Zipser LLP

(57) ABSTRACT

Cancer is treated via a coordinated treatment regimen that use various compounds and compositions that employ prime-boost vaccination in combination with immune modulatory treatment and biasing of an immune response towards a Th1 profile.

6 Claims, 20 Drawing Sheets

(56) References Cited

OTHER PUBLICATIONS

Marks et al., J. Biol. Chem. 295(29) 9823-9837 (2020 (PTO 892)).*
Akbar et al., Cell Reports 34, 108856, Mar. 16, 2021.*
Lo et al., BMC Genomics vol. 22, Article No. 116 (2021).*
Goel et al. (2004, J. Immunol. 173: 7358-7367).*
Khan et al. (2014, J. Immunol. 192: 5398-5405).*
Poosarla et al. (2017, Biotechn. Bioeng. 114(6): 1331-1342).*
Schreiber et al., "Cancer immunoediting: integrating immunity's roles in cancer suppression and promotion", Science, Mar. 25, 2011, vol. 331, pp. 1565-1570 (Cited from Specification).
Islamuddin et al., "Th1-Biased Immunomodulation and Therapeutic Potential of Artemisia annua in Murine Visceral Leishmaniasis", PLOS, neglected Tropical Diseases, Jan. 2015, vol. 9, No. 1, pp. 1-16 (Cited from Specification).
Klinman Dennis M, "Therapeutic Implications of Orally Delivered Immunomodulatory Oligonucleotides", Molecular Therapy, Feb. 1, 2015, vol. 23, No. 2, pp. 222-223 (Cited from Specification).
Langhans et al., "Ribavirin Exerts Differential Effects on Functions of Cd4+ Th1, Th2, and Regulatory T Cell Clones in Hepatitis C", Plos One, Jul. 2012, vol. 7, No. 7, pp. 1-9 (Cited from Specification).
Sanborn et al., "Phylogenetic analyses of melanoma reveal complex patterns of metastatic dissemination", PNAS, Sep. 1, 2015, vol. 112, No. 35, pp. 10995-11000.
Lundegaard et al., "NetMHC-3.0: accurate web accessible predictions of human, mouse and monkey MHC class I affinities for peptides of length 8-11", Nucleic Acids Research, May 7, 2008, vol. 36, pp. W509-W512.
Giudicelli et al., "IMGT/GENE-DB: a comprehensive database forhuman and mouse immunoglobulin and T cell receptor genes", Nucleic Acids Research, 2005, vol. 33, pp. D256-D261.
Lundegaard et al., "Accurate approximation method for prediction of class I MHC affinities for peptides of length 8, 10 and 11 using prediction tools trained on 9mers" Bioinformatics, 2008, vol. 24, No. 11, pp. 1397-1398.
International Preliminary Report on Patentability Chapter I received for PCT Application Serial No. PCT/US2019/028550 dated Nov. 5, 2020, 8 pages.
Office Action received in Taiwanese Patent Application Serial No. 108113912 dated May 28, 2020, 13 pages (Including English translation).
Lee et al., "In-situ diversification of immunity following vaccination targeting tumor neoepitopes; an integral component of combinatorial immunotherapy", European Journal of Cancer, 2019, 47 pages.
International Search Report and Written Opinion received in PCT Application Serial No. PCT/US2019/028550 received in Jun. 12, 2020, 14 pages.
Office Action received in Taiwanese Patent Application Serial No. 108113912 dated Sep. 17, 2020, 13 pages (Including English Translation).
Wolchok et al., "Guidelines for the Evaluation of Immune Therapy Activity in Solid Tumors: Immune-Related Response Criteria", Cancer Therapy: Clinical, Dec. 1, 2009, vol. 15, No. 23, pp. 7412-7420.
Eisenhauer et al., "New response evaluation criteria in solid tumours:Revised RECIST guideline (version 1.1)", European Journal of cancer, 2009, vol. 45, pp. 228-247.
International Search Report and Written Opinion received in PCT Application Serial No. PCT/US19/55054 received in Jan. 2, 2020, 14 pages.
Final Office Action received for U.S. Appl. No. 16/656,293 dated Oct. 22, 2021,20 pages.
Office Action received for Canadian Patent Application Serial No. 3093569, dated Oct. 6, 2021, 5 pages.
Extended European Search Report received for EP Patent Application Serial No. 19882224.9 dated Feb. 15, 2022, 10 pages.
Kabacaoglu et al., "Immune Checkpoint Inhibition for Pancreatic Ductal Adenocarcinoma: Current Limitations and Future Options", Frontiers in Immunology, vol. 9, Article 1878, Aug. 2018, pp. 1-24.
Non-Final Office Action received for U.S. Appl. No. 16/656,293 dated Feb. 4, 2022, 194 pages.
Kim et al., "IL-15 superagonist/IL-15RaSushi-Fc fusion complex (IL-15SA/ IL-15RaSu-Fc; AL T-803) markedly enhances specific sub-populations of N Kand memory CDS+ T cells, and mediates potent anti-tumor activity against murine breast and colon carcinomas", Oncotarget, vol. 7, No. 13, Feb. 18, 2016, pp. 16130-16145.
First Office Action received for Taiwanese Patent Application Serial No. 108113912 dated Apr. 14, 2022, 5 pages.
International Preliminary Report on Patentability received for PCT Application Serial No. PCT/US2019/055054 dated Apr. 21, 2022, 8 pages.
Final Office Action received for U.S. Appl. No. 16/656,293 dated Apr. 22, 2022, 116 pages.
Rhode PR, et al. "Cancer Immunol Res." Jan. 2016, vol. 4, pp. 49-60.
Boyerinas et al., "Antibody-dependent cellular cytotoxicity (ADCC) activity of a novel anti-PD-L1 antibody avelumab (MSB0010718C) on human tumor cells" Cancer Immunol Res , Oct. 2015, vol. 3 (10), pp. 1148-1157.
Mathios et al., "Therapeutic administration of IL-15 superagonist complex ALT-803 leads to long-term survival and durable antitumor immune response in a murine glioblastoma model", Int J Cancer. Jan. 1, 2016, vol. 138(1), pp. 187-194.
Fallon et al., "The immunocytokine NHS-IL12 as a potential cancer therapeutic", Oncotarget, Mar. 24, 2014, vol. 5, No. 7.
Jochems et al., "Analyses of functions of an anti-PD-L1/TGFβR2 bispecific fusion protein (M7824)" Oncotarget, Sep. 8, 2017, vol. 8, (No. 43), pp. 75217-75231.
Office Action received for Candian Patent Application Serial No. 3,093,569 dated Jul. 29, 2022, 5 pages.
Non Final Office Action received for U.S. Appl. No. 16/656,293 dated Jul. 6, 2021, 94 pages.

* cited by examiner

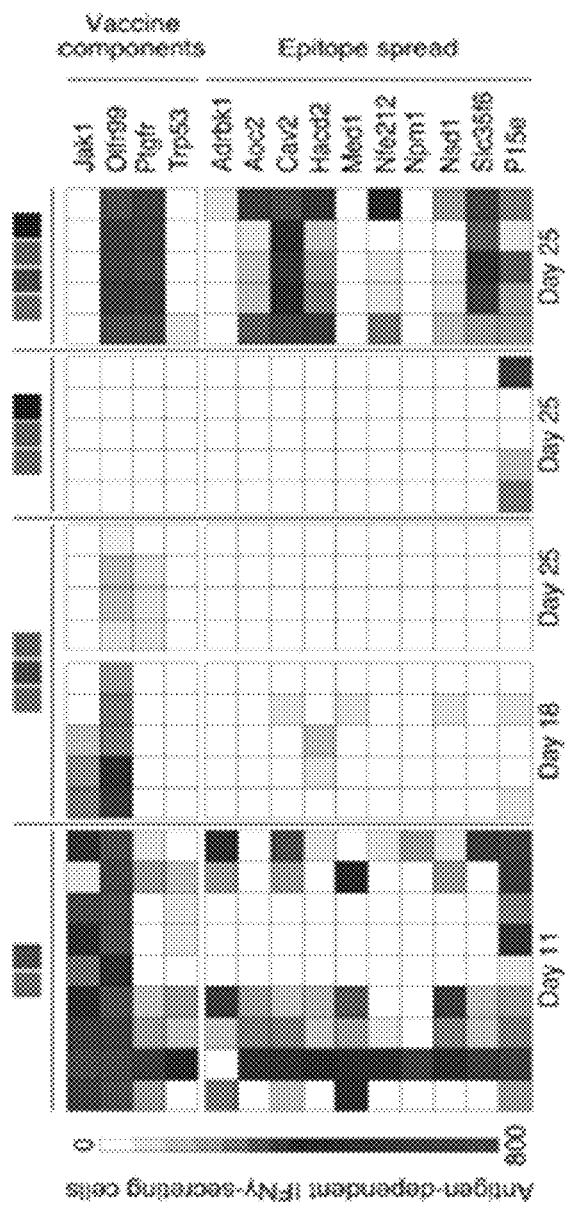
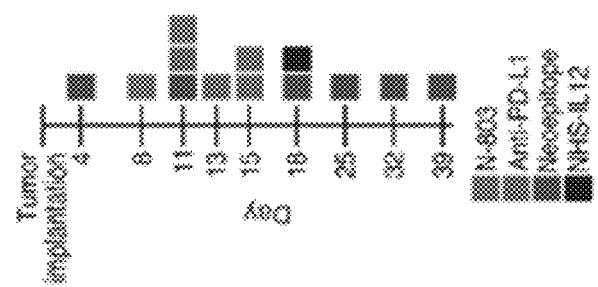
Fig. 7A
Fig. 7B

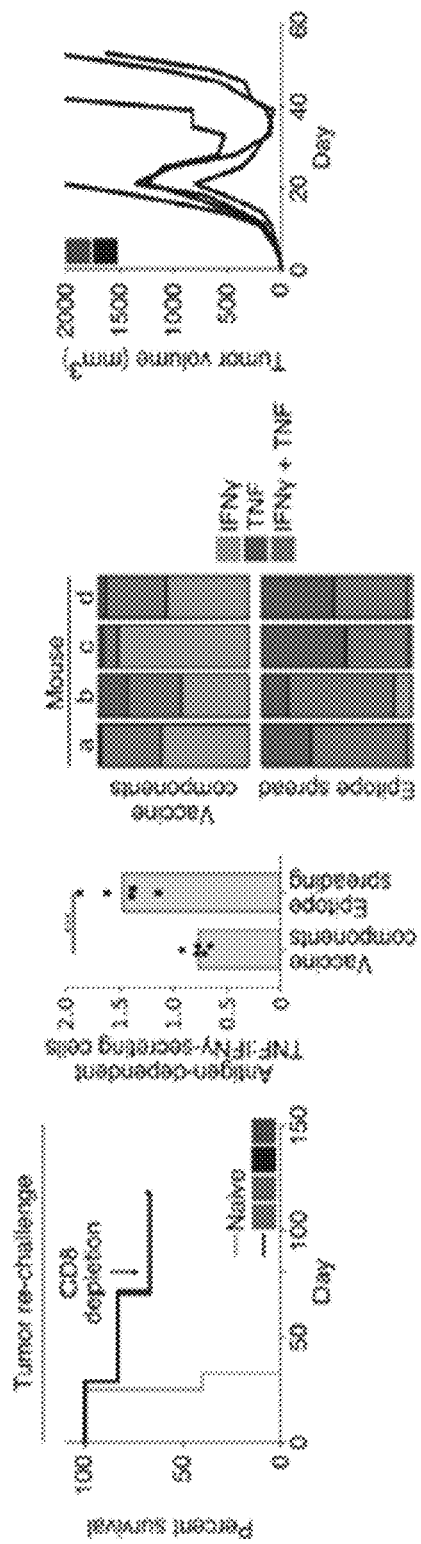

US 11,590,217 B2

NEOEPITOPE VACCINE AND IMMUNE STIMULANT COMBINATIONS AND METHODS

This application claims priority to our co-pending US provisional patent application with the Ser. No. 62/661,298, filed Apr. 23, 2018, which is incorporated by reference in its entirety herein.

FIELD OF THE INVENTION

The field of the invention is compositions and methods of cancer therapy, especially as it relates to protocols and compositions for cancer immunotherapy that utilize vaccine and immune modulators in a coordinated manner.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

The immune system has been described as playing a dual role in cancer as it can protect against cancer development by detecting and eliminating tumor cells, but also in that it can promote cancer progression by selection of tumor cells that escape immune destruction. This paradoxical role of the immune system in cancer is also known as cancer immunoediting (see e.g., Science. 2011; 331:1565-70). Cancer cells frequently employ various mechanisms to evade recognition and destruction by immune cells. For example, cancer cells can modulate the tumor microenvironment (TME) through recruitment of regulatory T cells (Tregs), myeloid-derived suppressor cells (MDSCs), and immunosuppressive macrophages (M2 macrophages). Cancer cells can also evade the immune system by down-regulating expression of certain MHC (major histocompatibility complex) molecules, which are deemed typically essential for T cells to recognize tumor-associated antigens (TAAs). Still further, cancer cells can secrete immune suppressive cytokines (e.g., TGF-β, IL-8) to establish a more immune suppressive environment.

To overcome at least some of the downregulating functions in the immune evasion of a tumor, various pharmaceutical agents have been tested with varying degree of success. For example, immune stimulants can be administered to increase an immune response to specific tumor antigens. Among other immune stimulants, certain cytokines and derivatives are often used and include IL-2, IL-12, or IL-15, and chimeric forms thereof such as ALT-803 (see e.g., Altor BioScience Corporation, 2810 North Commerce Parkway, Miramar, Fla. 33025; ALT-803 FACT SHEET) or NHS-IL-12 (see e.g., Oncotarget 2014, Vol. 5, No. 7, 1869-1884). While increasing some of the parameters in an immune response, administration of such compounds per se has not been proven to be therapeutically effective in eradication of a tumor. In yet another known approach, various checkpoint inhibitors have been used in the treatment of cancer, and in some cases yielded remarkable results. However, as with the cytokine-type immune stimulants, consistent responses have been elusive, especially across different types of cancer. In other known approaches, tumor vaccines have been employed to generate an immune response against a tumor specific or tumor associated antigen. Once more, notable immune responses were observed in some cases. However, immune stimulation with vaccine compositions is still often associated with suppression of an immune response in a tumor. To improve immune response and reduce immune suppression, timed immunotherapy has been described to address immune editing as taught in WO 2018005973. Such coordinated therapy advantageously addresses immune escape from various angles. However, such therapy is often lengthy and requires multiple treatment agents and a complex treatment regimen.

Consequently, there is still a need to provide treatment compositions and methods that improve cancer immune therapy, and especially a therapy that is conceptually simple and effective using a minimum of therapeutic agents.

SUMMARY OF THE INVENTION

The inventive subject matter is directed to various compositions and methods of cancer immune therapy, in which various pharmaceutical compositions are administered to the patient to so elicit a therapeutically effective response. Most preferably, such methods include prime/boost administration of a cancer vaccine with concurrent and overlapping immune stimulation and checkpoint inhibition regimes. It is further preferred that the so generated immune response is further modified/enhanced by administration of a pharmaceutical that triggers a Th1 bias of the immune response.

In one aspect of the inventive subject matter, the inventors contemplate a method of stimulating an immune response in an individual against a (typically solid) tumor. The method includes a step of subjecting the individual to a timed treatment combination that includes a prime-boost vaccination regime, an immune stimulation regimen, a checkpoint inhibition regimen, and a Th1 stimulation. Most preferably, the immune stimulation regimen commences after the prime vaccination, the checkpoint inhibition regimen commences after the immune stimulation regimen, and the Th1 stimulation commences after the boost vaccination or subsequent administration of the vaccine composition.

While not limiting to the inventive subject matter, it is contemplated that the prime-boost vaccination regime comprises administration of a vaccine composition that elicits an immune response towards at least one of a tumor associated antigen and a tumor specific antigen, and it is generally preferred that the vaccine composition comprises a bacterial, a yeast, or a viral vaccine composition. In further typical embodiments, the prime-boost vaccination regime comprises administration of the vaccine composition in weekly intervals.

It is further contemplated that the immune stimulation regimen comprises administration of at least one of IL-2, IL-12, IL-15, IL-21 or a derivative thereof (which may include a targeting antibody, or an antibody fragment), and an especially preferred derivative is ALT-803. For example, the immune stimulation regimen may comprise administration of at least one of IL-2, IL-12, IL-15, IL-21 or a derivative thereof in 3-5 day intervals. With respect to checkpoint inhibition it is contemplated that the checkpoint inhibition regimen comprises administration of an anti PD1 antibody, an anti-PD-L1 antibody, and/or an anti-CTLA4 antibody, which is preferably performed in 1-3 day intervals.

Contemplated Th1 stimulations typically comprise administration of a cytokine or small molecule drug that biases an immune response towards a Th1 response. Therefore, especially preferred cytokines include IL-12 or a derivative thereof (e.g., comprising an antibody portion that binds to a tumor cell or a necrotic component of a tumor cell).

In further contemplated aspects, the immune stimulation regimen and the checkpoint inhibition will regimen overlap, and/or the immune stimulation regimen, the checkpoint inhibition regimen, and the Th1 stimulation are at least initiated during the prime-boost vaccination regime.

In another aspect of the inventive subject matter, the inventors contemplate a method of treating a tumor in an individual that includes the following steps: (a) subjecting the individual to a vaccination regimen with a vaccine composition to elicit an immune response towards at least one of a tumor associated antigen and a tumor specific antigen, wherein the vaccination regimen comprises at least a first and a second administration of a vaccine composition; (b) subjecting the individual to an immune stimulation regimen after the first administration of the vaccine composition, wherein the immune stimulation regimen comprises at least a first and a second administration of an immune stimulatory composition; (c) subjecting the individual to a checkpoint inhibition regimen after the first administration of the immune stimulatory composition, wherein the checkpoint inhibition regimen comprises at least a first and a second administration of a checkpoint inhibitor; and (d) subjecting the individual to Th1 stimulation after the second or subsequent administration of the vaccine composition, wherein the Th1 stimulation comprises administration of a compound that biases an immune response towards a Th1 response.

Most typically, the first and the second administration of the vaccine composition, and optionally the second administration and a subsequent administration of the vaccine composition, are between 5 and 10 days apart, and/or the first administration of the immune stimulatory composition is between the first and second administration of the vaccine composition. It is further contemplated that the first administration of the checkpoint inhibitor is between the first and second administration of the immune stimulatory composition, or concurrent with or after administration of the second administration of the vaccine composition, and/or that the immune stimulation regimen and the checkpoint inhibition regimen are performed between the first and a last administration of the vaccine composition. Therefore, the immune stimulation regimen and the checkpoint inhibition regimen may overlap. In further contemplated embodiments, the first and the second administration of the immune stimulatory composition are between 3-5 days apart, and/or the first and the second administration of the checkpoint inhibitor are between 1-3 days apart. As noted above, it is also contemplated that the compound that biases the immune response towards the Th1 response further comprises an antibody or antibody fragment that binds to a tumor cell or a component of a necrotic cell.

Consequently, it should be appreciated that the inventors also contemplate a coordinated use of a vaccine composition, an immune stimulatory composition, a checkpoint inhibitor, and a compound that biases an immune response towards a Th1 response. In such use, it is generally preferred that the immune stimulatory composition is administered after administration of a first dose of the vaccine composition, that the checkpoint inhibitor is administered after a first dose of the immune stimulatory composition, and that the compound that biases the immune response towards the Th1 response is administered after a second or subsequent administration of the vaccine composition.

Preferably, the vaccine composition elicits an immune response towards at least one of a tumor associated antigen and a tumor specific antigen, and/or comprises a bacterial vaccine, a yeast vaccine, or a viral vaccine. Moreover, it is generally preferred that the immune stimulatory composition comprises a cytokine or a cytokine derivative (e.g., at least one of IL-2, IL-12, IL-15, IL-21 or a derivative thereof where the derivative thereof comprises a targeting antibody, or an antibody fragment, and/or ALT-803). Optionally, the checkpoint inhibitor comprises an antibody binding to PD1, PD-L1, or CTLA4. Further optionally, it is generally preferred that the compound that biases the immune response towards the Th1 response comprises IL-12, optionally coupled to an antibody or fragment thereof that binds to a tumor cell or a component of a necrotic tumor cell (e.g., NHS IL-12). In further contemplated uses, the vaccine composition is administered using a weekly schedule, the immune stimulatory composition is administered using a 3-5 day schedule, and the checkpoint inhibitor is administered using a 1-3 day schedule.

Various objects, features, aspects, and advantages of the inventive subject matter will become more apparent from the following detailed description, along with the accompanying drawing.

DETAILED DESCRIPTION

Figure 1:
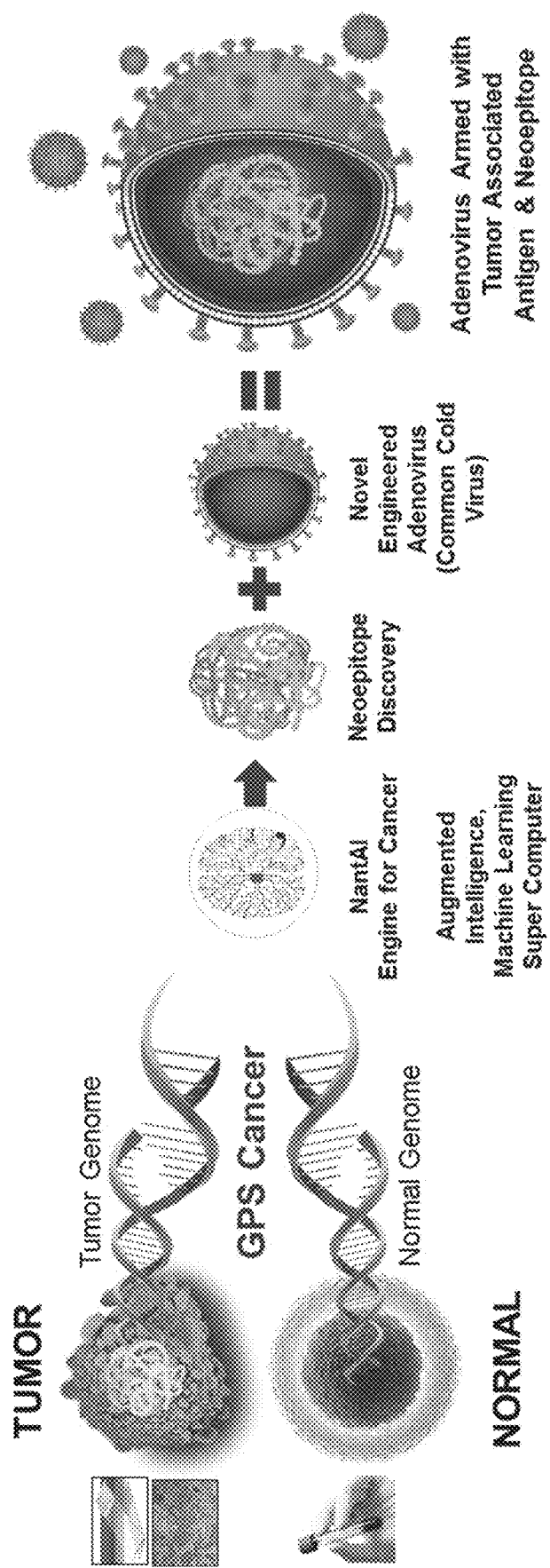
FIG. 1 is a schematic illustration of a personalized vaccine preparation used in the inventive subject matter.

The inventors have discovered that cancer immune therapy can be administered using a coordinated orchestration of a combination of certain immunotherapeutic agents to so elicit an effective anti-tumor response in a mammal. Preferably, such orchestrated treatments are based on a prime/boost vaccination regimen that includes an immune stimulation phase using one or more immune stimulatory cytokines and checkpoint inhibition phase using one or more checkpoint inhibitors, before the so elicited immune response is further maintained and/or modified towards a Th1 response.

Thus, it is also contemplated that immune therapy using a prime/boost regiment with cancer vaccine can be significantly improved by stimulating the immune system after the prime vaccination with immune stimulatory cytokines, and by further modulating suppressive signals with checkpoint inhibitors, preferably at or during the boost phase of the vaccination. Stimulation and checkpoint inhibition are continued during the boost phase, and the so elicited immune response is then supported and/or further modulated towards a Th1 response by administration of a second immunostimulatory cytokine, preferably in a tumor targeted manner.

Notably, such protocol provided significant therapeutic effect as is further demonstrated in more detail below. As the immunomodulation in contemplated treatments are independent of the particular tumor type, and as the vaccine is specific to a patient's specific tumor, it should be recognized that contemplated compositions and methods will be suitable for a variety of tumors, including solid tumors, soft tissue tumors, and lymphatic tumors.

As used herein, the term "tumor" refers to, and is interchangeably used with one or more cancer cells, cancer tissues, malignant tumor cells, or malignant tumor tissue, that can be placed or found in one or more anatomical locations in a human body. As used herein, the term "bind" refers to, and can be interchangeably used with a term "recognize" and/or "detect", an interaction between two molecules with a high affinity with a $K_D$ of equal or less than $10^{-6}$M, or equal or less than $10^{-7}$M. As used herein, the term "provide" or "providing" refers to and includes any acts of manufacturing, generating, placing, enabling to use, or making ready to use.

For example, with respect to the vaccination regimen it should be appreciated that the type and content of the vaccine composition to elicit an immune response towards at least one of a tumor associated antigen and a tumor specific antigen may vary considerably. Consequently, all manners of providing an immunogen to an individual are deemed suitable and include DNA vaccines, peptide vaccines, and especially recombinant vaccines. Likewise, the content of the vaccines may vary considerably and may include a tumor associated antigen or fragment thereof (e.g., MUC1, brachyury, CEA, etc.), a tumor specific antigen or fragment thereof (e.g., PSA, PSMA, HER2, etc.), and particularly tumor and patient specific neoantigens (i.e., neoepitopes). As used herein, the tumor-associated antigen refers any antigen that can be presented on the surface of the tumor cells, which includes an inflammation-associated peptide antigen, a tumor associated peptide antigen, a tumor specific peptide antigen, and a cancer neoepitope.

In some embodiments, the tumor associated antigen is a tumor-specific, patient-specific neoepitope. It is contemplated that patient- and tumor-specific neoantigens or neoepitopes can be identified via analyzing and comparing omics data from diseased tissue and healthy tissue of a patient, (e.g., via whole genome sequencing and/or exome sequencing, etc.) as is described in US20120059670 and US20120066001. For example, the tumor associated antigens and neoepitopes (which are typically patient-specific and tumor-specific) can be identified from the omics data obtained from the cancer tissue of the patient or normal tissue (of the patient or a healthy individual), respectively. Omics data of tumor and/or normal cells preferably comprise a genomic data set that includes genomic sequence information. Most typically, the genomic sequence information comprises DNA sequence information that is obtained from the patient (e.g., via tumor biopsy), most preferably from the tumor tissue (diseased tissue) and matched healthy tissue of the patient or a healthy individual. For example, the DNA sequence information can be obtained from a pancreatic cancer cell in the patient's pancreas (and/or nearby areas for metastasized cells), and a normal pancreatic cells (non-cancerous cells) of the patient or a normal pancreatic cells from a healthy individual other than the patient.

In one especially preferred aspect of the inventive subject matter, DNA analysis is performed by whole genome sequencing and/or exome sequencing (typically at a coverage depth of at least 10×, more typically at least 20×) of both tumor and matched normal sample. Alternatively, DNA data may also be provided from an already established sequence record (e.g., SAM, BAM, FASTA, FASTQ, or VCF file) from a prior sequence determination. Therefore, data sets may include unprocessed or processed data sets, and exemplary data sets include those having BAM format, SAM format, FASTQ format, or FASTA format. However, it is especially preferred that the data sets are provided in BAM format or as BAMBAM diff objects (see e.g., US2012/0059670A1 and US2012/0066001A1). Moreover, it should be noted that the data sets are reflective of a tumor and a matched normal sample of the same patient to so obtain patient and tumor specific information. Thus, genetic germ line alterations not giving rise to the tumor (e.g., silent mutation, SNP, etc.) can be excluded such that the neoepitope is filtered against known human SNP and somatic variations. Of course, it should be recognized that the tumor sample may be from an initial tumor, from the tumor upon start of treatment, from a recurrent tumor or metastatic site, etc. In most cases, the matched normal sample of the patient may be blood, or non-diseased tissue from the same tissue type as the tumor.

The so obtained neoepitopes may then be subject to further detailed analysis and filtering using predefined structural and expression parameters, and sub-cellular location parameters. For example, it should be appreciated that neoepitope sequences are only retained provided they will meet a predefined expression threshold (e.g., at least 20%, 30%, 40%, 50%, or higher expression as compared to normal) and are identified as having a membrane associated location (e.g., are located at the outside of a cell membrane of a cell). Further contemplated analyses will include structural calculations that delineate whether or not a neoepitope or a tumor associated antigen, or a self-lipid is likely to be solvent exposed, presents a structurally stable epitope, etc. Further details on identification of patient-specific neoantigens and/or cancer-specific, patient-specific neoantigens are described in detail in the international patent application No. PCT/US16/56550.

Moreover, it is especially contemplated that the tumor-related antigen is a high-affinity binder to at least one MHC Class I sub-type or at least one MHC Class II sub-type of an HLA-type of the patient, which may be determined in silico using a de Bruijn graph approach as, for example, described in WO 2017/035392, or using conventional methods (e.g., antibody-based) known in the art. The binding affinity of the human disease-related antigen is tested in silico to the determined HLA-type. The preferred binding affinity can be measured by lowest KD, for example, less than 500 nM, or less than 250 nM, or less than 150 nM, or less than 50 nM, for example, using NetMHC. Most typically, the HLA-type determination includes at least three MHC-I sub-types (e.g., HLA-A, HLA-B, HLA-C, etc.) and at least three MHC-II sub-types (e.g., HLA-DP, HLA-DQ, HLA-DR, etc.), preferably with each subtype being determined to at least 4-digit depth. It should be appreciated that such approach will not only identify specific neoantigens that are genuine to the patient and tumor, but also those neoantigens that are most likely to be presented on a cell and as such most likely to elicit an immune response with therapeutic effect.

Of course, it should be appreciated that matching of the patient's HLA-type to the patient- and cancer-specific neoantigen can be done using systems other than NetMHC, and suitable systems include NetMHC II, NetMHCpan, IEDB Analysis Resource (URL immuneepitope.org), RankPep, PREDEP, SVMHC, Epipredict, HLABinding, and others (see e.g., J Immunol Methods 2011; 374:1-4). In calculating the highest affinity, it should be noted that the collection of neoantigen sequences in which the position of the altered amino acid is moved (supra) can be used. Alternatively, or additionally, modifications to the neoantigens may be implemented by adding N- and/or C-terminal modifications to further increase binding of the expressed neoantigen to the patient's HLA-type. Thus, neoantigens may be native as identified or further modified to better match a particular HLA-type.

Moreover, where desired, binding of corresponding wild type sequences (i.e., neoantigen sequence without amino acid change) can be calculated to ensure high differential affinities. For example, especially preferred high differential affinities in MEW binding between the neoantigen and its corresponding wild type sequence are at least 2-fold, at least 5-fold, at least 10-fold, at least 100-fold, at least 500-fold, at least 1000-fold, etc.

In addition, the omics information (especially where the omics information comprises whole genome sequencing or exome sequencing, RNA sequence and transcription data, and (preferably quantitative) proteomics information) can also be used to determine the status of various cell signaling pathways. Such pathway information, and especially in conjunction with mutational information, may reveal further druggable targets within a cell that are independent from anatomical features of the tumor (e.g., presence of HER2 signaling in a non-breast cancer). Particularly preferred pathway analyses that are based on omics information include those described in WO 2011/139345, WO 2013/062505, WO 2014/193982, WO 2014/059036, WO 2014/210611, WO 2015/184439, and WO 2016/118527. Viewed from a different perspective, omics data in contemplated treatments and uses will be employed to both, inform generation of immune therapeutic compositions as well as inform selection of chemotherapeutic drugs based on pathway information rather than tumor type and location. Therefore, suitable omics data include whole genome sequencing data, exome sequencing data, RNA sequence and transcription data, and proteomics data (e.g., quantitative proteomics data from mass spectroscopic analyses).

In some embodiments, the tumor associated antigen or neoepitopes can be a polytope. As used herein, a polytope refers a tandem array of two or more antigens (or neoepitopes) expressed as a single polypeptide. Preferably, two or more human disease-related antigens are separated by a linker or spacer peptides. Any suitable length and order of peptide sequence for the linker or the spacer can be used. However, it is preferred that the length of the linker peptide is between 3-30 amino acids, preferably between 5-20 amino acids, more preferably between 5-15 amino acids. Also inventors contemplates that glycine-rich sequences (e.g., gly-gly-ser-gly-gly, etc.) are preferred to provide flexibility of the polytope between two antigens.

Figure 2:
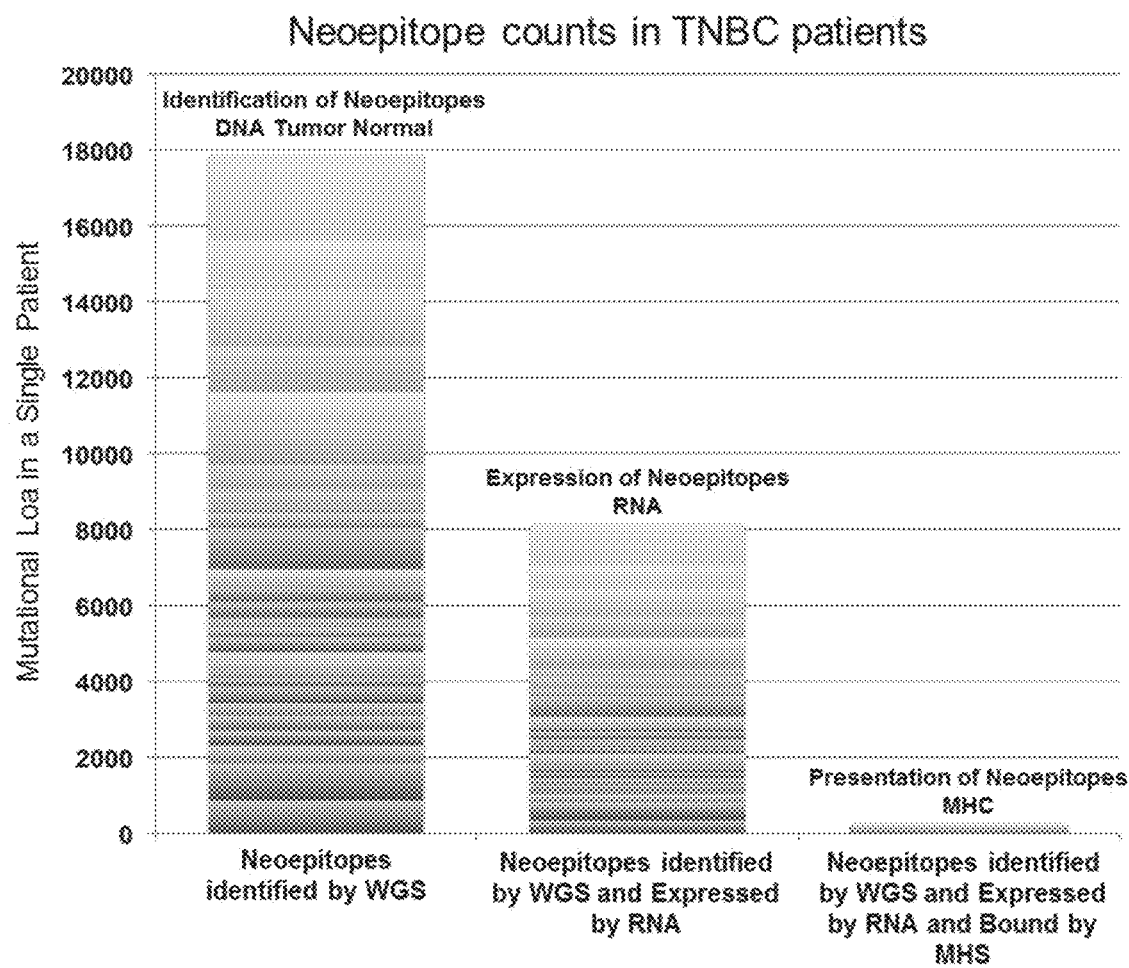
FIG. 2 is a graph depicting exemplary results for patient neoepitope filtering using expression and calculated MHC binding.

The notable reduction in potentially useful neoepitopes as described above is exemplarily shown in FIG. 1 where a patients tumor tissue is compared using the same patient's normal tissue using omics analysis and neoepitope discovery. Once identified, an adenovirus is then genetically engineered to include an expression cassette that includes nucleic acid segments that encode one or more neoepitopes of the patient. Such modified virus can then be used as a recombinant viral vaccine. FIG. 2 exemplarily illustrates a selection process in which all neoepitopes identified by omics analysis (left bar) are first filtered by expression level. Here, non-expressed neoepitopes are eliminated, resulting in a substantial reduction in potential neoepitopes (middle bar). These filtered neoepitopes are further filtered against the patients MHC type, and as can be seen from the Figure (right bar), the number of neoepitopes that can be presented by the patient's antigen presenting cells is once more dramatically reduced. The neoepitopes can then be used in therapy for example in a recombinant virus/recombinant expression system.

In especially contemplated aspects, a nucleic acid sequence encoding one or more tumor-associated antigen(s) and/or neoepitopes can be placed in an expression vector. The recombinant nucleic acid is then inserted into an expression vector such that the nucleic acid can be delivered to an antigen presenting cell (e.g., dendritic cells, etc.) of the patient, or to transcribe the nucleic acid sequence in bacteria or yeast so that the recombinant protein encoded by the nucleic acid sequence can be, as a whole, or as fragments, delivered to the antigen presenting cell. Any suitable expression vectors that can be used to express protein are contemplated. Especially preferred expression vectors may include those that can carry a cassette size of at least 1 k, preferably 2 k, more preferably 5 k base pairs.

Thus, in one embodiment, a preferred expression vector includes a viral vector (e.g., non-replicating recombinant adenovirus genome, optionally with a deleted or non-functional E1 and/or E2b gene). Where the expression vector is viral vector (e.g., an adenovirus, and especially AdV with E1 and E2b deleted), it is contemplated that the recombinant viruses including the recombinant nucleic acid may then be individually or in combination used as a therapeutic vaccine in a pharmaceutical composition, typically formulated as a sterile injectable composition with a virus titer of between $10^6$-$10^{13}$ virus particles, and more typically between $10^9$-$10^{13}$ virus particles per dosage unit. For example, the virus vaccine can be formulated with a virus titer at least $10^6$ virus particles/day, or at least $10^8$ virus particles/day, or at least $10^{10}$ virus particles/day, or at least $10^{11}$ virus particles/day. Alternatively, virus may be employed to infect patient (or other HLA matched) cells ex vivo and the so infected cells are then transfused to the patient.

In still further embodiments, the expression vector can also be a bacterial vector that can be expressed in a genetically engineered bacterium, which expresses endotoxins at a level low enough not to cause an endotoxic response in human cells and/or insufficient to induce a CD-14 mediated sepsis when introduced to the human body. One exemplary bacteria strain with modified lipopolysaccharides includes ClearColi® BL21 (DE3) electrocompetent cells. This bacteria strain is BL21 with a genotype F-ompT hsdSB (rB-mB) gal dcm lon λ(DE3 [lacI lacUV5-T7 gene 1 indI sam7 nin5]) msbA148 ΔgutQΔkdsD ΔlpxLzLΔlpxMΔpagPΔlpxPΔeptA. In this context, it should be appreciated that several specific deletion mutations (ΔgutQ ΔkdsD ΔlpxL ΔlpxMΔpagPΔlpxPΔeptA) encode the modification of LPS to Lipid IVA, while one additional compensating mutation (msbA148) enables the cells to maintain viability in the presence of the LPS precursor lipid IVA. These mutations result in the deletion of the oligosaccharide chain from the LPS. More specifically, two of the six acyl chains are deleted. The six acyl chains of the LPS are the trigger which is recognized by the Toll-like receptor 4 (TLR4) in complex with myeloid differentiation factor 2 (MD-2), causing activation of NF-κB and production of proinflammatory cytokines. Lipid IVA, which contains only four acyl chains, is not recognized by TLR4 and thus does not trigger the endotoxic response. While electrocompetent BL21 bacteria is provided as an example, the inventors contemplates that the genetically modified bacteria can be also chemically competent bacteria. Alternatively, or additionally, the expression vector can also be a yeast vector that can be expressed in yeast, preferably, in *Saccharomyces cerevisiae* (e.g., GI-400 series recombinant immunotherapeutic yeast strains, etc.). Of course, it should be appreciated that recombinant nucleic acids contemplated herein need not be limited to viral, yeast, or bacterial expression vectors, but may also include DNA vaccine vectors, linearized DNA, and mRNA, all of which can be transfected into suitable cells following protocols well known in the art.

Moreover, it should be recognized that the vaccine composition may change over the course of the vaccination regimen, in terms of formulation and in terms of antigen composition. For example, a prime vaccination may be performed using a recombinant bacterial or yeast expression system as described above, which is then followed in the boost phase using with an adenoviral vaccination. Additionally, the vaccination regimen may also use different routes of administration, including subcutaneous or intramuscular administration of a bacterial or yeast vaccine composition, and an intratumoral or intravenous administration of an adenoviral vaccine composition. Similarly, in less preferred aspects, the prime vaccine composition may include both tumor associated antigens and neoepitopes, while the boost vaccination may include or encode only neoepitopes as the immunogenic agent.

Still further, it is contemplated that the vaccine regimen may use various timelines for administration. However, it is generally contemplated that the timing of prime/boost will follow an anticipated timing of immune response with respect to antigen processing and presentation and T cell stimulation and proliferation. Therefore, the vaccine compositions will at least initially be administered at least 2 days apart, more typically within a window of 3-5 days, or 5-7 days, or 7-10 days, or 10-14 days, and in some cases even longer. For subsequent administrations in the boost phase (e.g., fourth, fifth, etc. administration), the interval may be longer, including several weeks, months, or even years. In some embodiments, the dose of the virus formulation can be gradually increased during the schedule, or gradually decreased during the schedule. In still other embodiments, several series of administration of virus formulation can be separated by an interval (e.g., one administration each for 3 consecutive days and one administration each for another 3 consecutive days with an interval of 7 days, etc.).

With respect to contemplated immune stimulation regimens, it is generally preferred that such regimen comprises at least a first and a second administration of one or more immune stimulatory compositions, and it is generally preferred that the immune stimulatory composition comprises an immune stimulatory cytokine. For example, especially preferred cytokines include various interleukins, and particularly IL-2, IL-12, IL-15, IL-17, IL-21, as well as other cytokines including Th1 cytokines (e.g., IFN-γ, TNFα, etc.). Suitable dosages for the immune stimulation will typically be within the range of clinically acceptable dosages, which art well known in the art. Moreover, it is further contemplated that the immune stimulatory compositions may also include modified forms of the above noted proteins, and especially modified forms include those that increase serum half life time and/or reduce toxicity. For example, contemplated immune stimulating compositions may include truncated IL-2 that lacks the PEP portion, or ALT-803, which is an IL-15 based chimeric protein complex with IL-15 superagonist function. Still further contemplated immune stimulatory compounds may also be target specific, for example, by coupling to an antibody or portion thereof, wherein the antibody typically binds a tumor epitope, a neoepitope, or a component of a necrotic cell (e.g., dsDNA, histones, etc.). Once more, it should be noted that suitable dosages for the immune stimulation using such compounds will typically be within the range of clinically acceptable dosages, which art well known in the art.

Alternatively, or additionally, further contemplated immune stimulatory compounds include various TLR ligands and/or NOD ligands that enhance an immune response. For example, suitable TLR ligands include TLR2, TLR3, TLR4, TLR7, or TLR8, and especially include mRNA, dsDNA, ssRNA, CpG, glycolipids, etc. In still further contemplated aspects, immune stimulatory compounds may also include an OX40 agonistic antibody. Thus, numerous immune stimulatory compounds are deemed suitable, and all reasonable combinations thereof.

Of course, it should be recognized that the immune stimulatory compounds may change over the course of the treatment regimen, both in terms of type and the dosage of the immune stimulatory compounds. For example, initial stimulation maybe may be performed using more acute effect compounds (e.g., IL-2, IL-15), while subsequent administrations may employ immune stimulatory compounds with longer lasting effects (e.g., ALT-803). On the other hand, immune stimulatory compounds may also be administered in a target specific manner as noted above to reduce systemic (toxic) effects. The immune stimulatory regimen may use different routes of administration, including subcutaneous or intramuscular administration, however, intratumoral or intravenous administration are particularly preferred.

Still further, it is contemplated that the immune stimulatory regimen may use various timelines for administration. However, it is generally contemplated that the first administration will be after the prime administration of the vaccine as already noted above. Subsequent administrations will generally be in relatively rapid succession to elicit a substantially continuous stimulatory effect. Therefore, the immune stimulatory compounds will be administered about 1 day apart, more typically within a window of 1-2 days, or 2-3 days, or 1-3 days, or 2-4 days, and in some cases even longer intervals. For still later administrations (e.g., after the vaccine boost phase), the interval may be longer, including several weeks, months, or even years.

It is still further generally preferred that the immune stimulatory compounds are at least administered within the prime/boost vaccine regimen, and that the immune stimulatory regimen overlaps to at least some degree with a checkpoint inhibition regimen as described in more detail below. While not limiting to the inventive subject matter, it is believed that upon administration of the prime vaccination, an immune stimulatory phase that supports immune cell activation and a regimen that reduces checkpoint inhibition will modulate the immune system to provide an optimum response to the prime and contemporaneous/subsequent boost phase.

Therefore, it is generally preferred that the checkpoint inhibition regimen comprises at least a first and a second administration of a checkpoint inhibitor, and all known checkpoint inhibitors are deemed suitable for use herein. For example, suitable checkpoint inhibitors include those that interfere with signaling through PD-1 (e.g., pembrozilumab, nivolumab), PD-L1 (e.g., atezolizumab, avelumab, durvalumab), and/or CTLA4 (e.g., ipilimumab). There are numerous such inhibitors known in the art and all of those are deemed suitable for use herein. Suitable dosages for the immune stimulation will typically be within the range of clinically acceptable dosages, which are well known in the art. Likewise, where a tumor secrets soluble ligands to checkpoint receptors, it is contemplated that antibodies scavenging such soluble factors may be used to reduce adverse effects of such soluble forms.

As noted above, it is contemplated that the checkpoint inhibition regimen may employ various timelines for administration. However, it is generally contemplated that the first administration will be after the first administration of the vaccine and also after the first administration of the immune stimulatory compound. Thus, the immune stimulation and checkpoint inhibition will at least partially overlap. Subsequent administrations will generally be in relatively rapid succession to elicit a substantially continuous stimulatory effect. Therefore, the checkpoint inhibitors will be administered about 1 day apart, more typically within a window of 1-2 days, or 2-3 days, or 1-3 days, or 2-4 days, and in some cases even longer intervals. For still later administrations (e.g., after the vaccine boost phase), the interval may be longer, including several weeks, months, or even years.

With respect to the administration of the compound that biases the immune response towards a Th1 response and/or maintains an immune response against the tumor antigen with development of immune memory, it is generally preferred that the compound is a cytokine, and especially IL-12. Most preferably, to increase the site specificity and serum half-life of the IL-12, it is contemplated that the IL-12 is conjugated to an antibody or portion thereof, wherein the antibody binds to a tumor antigen, a tumor neoepitope, or a component of a necrotic cell. Thus, especially preferred compounds include NHS IL-12 and derivatives thereof. Alternatively, various other compounds can be used, including plant based compositions (e.g., *PLoS Negl Trop Dis.* 2015 January; 9(1): e3321), orally delivered deoxunucleotides (e.g., *Molecular Therapy*, Vol. 23, Issue 2, 222-223), ribavirin (e.g., *PLoS One.* 2012; 7(7): e42094.), and less preferably IL-4 and IL-10.

Administration of such compounds will generally follow dosages well known in the art, and all such dosages are deemed suitable for use herein. As noted above, it is contemplated that the Th1 stimulation/immune support may employ various timelines for administration. However, it is generally contemplated that the first administration will be after the second or subsequent administration of the vaccine and also after the administrations of the immune stimulatory compound and checkpoint inhibitor. Thus, the Th1 stimulation will typically coincide with the boost phase of vaccination, and most typically provide a support function that maintains the immune stimulation. Subsequent administrations will generally be in relatively slow succession to maintain a continuous stimulatory effect. Therefore, the compounds that stimulate Th1 will be administered, where desired, about 3 day apart, more typically within a window of 2-5 days, or 5-7 days, or 7-14, and in some cases even longer intervals. For still later administrations (e.g., with further vaccine boost administrations), the interval may be longer, including several weeks, months, or even years.

Of course, it should be appreciated that contemplated treatments may further include other therapeutic compositions that complement or otherwise support the methods described herein. For example, contemplated methods may include administration of autologous or heterologous NK cells to a patient, and particularly NK cells that are genetically modified to exhibit less inhibition. For example, the genetically modified NK cell may be a NK-92 derivative that is modified to have a reduced or abolished expression of at least one killer cell immunoglobulin-like receptor (KIR), which will render such cells constitutively activated. Of course, it should be noted that one or more KIRs may be deleted or that their expression may be suppressed (e.g., via miRNA, siRNA, etc.), including KIR2DL1, KIR2DL2, KIR2DL3, KIR2DL4, KIR2DL5A, KIR2DL5B, KIR2DS1, KIR2DS2, KIR2DS3, KIR2DS4, KIR2DS5, KIR3DL1, KIR3DL2, KIR3DL3, and KIR3DS1. Such modified cells may be prepared using protocols well known in the art. Alternatively, such cells may also be commercially obtained from NantKwest as aNK cells (activated natural killer cells). Such cells may then be further modified to express the co-stimulatory molecules as further discussed below. In addition, contemplated NK cells suitable for use herein also include those that have abolished or silenced expression of NKG2A, which is an activating signal to Tregs and MDSCs.

Alternatively, the genetically engineered NK cell may also be an NK-92 derivative that is modified to express a high-affinity Fcγ receptor (CD16-158V). Sequences for high-affinity variants of the Fcγ receptor are well known in the art, and all manners of generating and expression are deemed suitable for use herein. Expression of such receptor is believed to allow specific targeting of tumor cells using antibodies produced by the patient in response to the treatment contemplated herein, or supplied as therapeutic antibodies, where those antibodies are specific to a patient's tumor cells (e.g., neoepitopes), a particular tumor type (e.g., her2neu, PSA, PSMA, etc.), or antigens associated with cancer (e.g., CEA-CAM). Advantageously, such cells may be commercially obtained from NantKwest as haNK cells (high-affinity natural killer cells) and may then be further modified (e.g., to express co-stimulatory molecules).

In further aspects, genetically engineered NK cells may also be genetically engineered to express a chimeric T cell receptor. In especially preferred aspects, the chimeric T cell receptor will have an scFv portion or other ectodomain with binding specificity against a tumor associated antigen, a tumor specific antigen, and/or a neoepitope of the patient as determined by the omics analysis. As before, such cells may be commercially obtained from NantKwest as taNK cells (target-activated natural killer cells') and further modified as desired. Where the cells have a chimeric T cell receptor engineered to have affinity towards a cancer associated antigen or neoepitope, it is contemplated that all known cancer associated antigens and neoepitopes are considered appropriate for use. For example, tumor associated antigens include CEA, MUC-1, CYPB1, PSA, Her-2, PSA, brachyury, etc.

Moreover, it should be noted that the methods and uses contemplated herein also include cell based treatments with cells other than (or in addition to) NK cells. For example, suitable cell based treatments include T cell based treatments. Among other options, it is contemplated that one or more features associated with T cells (e.g., CD4+ T cells, CD8+ T cells, etc.) can be detected. More specifically, contemplated omics analysis can identify specific neoepitopes (e.g., 8-mers to 12-mers for MHC I, 12-mers to 25-mers for MHC II, etc.) that can be used for the identification of neoepitope reactive T cells bearing a specific T cell receptor against the neoepitopes/MHC protein complexes. Thus, the method can include harvesting the neoepitope reactive T cells. The harvested T cells can be grown or expanded (or reactivated where exhausted) ex vivo in preparation for reintroduction to the patient. Alternatively, the T cell receptor genes in the harvested T cells can be isolated and transferred into viruses, or other adoptive cell therapies systems (e.g., CAR-T, CAR-TANK, etc.). Beyond neoepitopes, the omics analyses can also provide one or more tumor associated antigens (TAAs). Therefore, one can also harvest T cells that have receptors that are sensitive to the TAAs identified from these analyses. These cells can be grown or cultured ex vivo and used in a similar therapeutic manner as discussed above. The T cells can be identified by producing synthetic versions of the peptides and bind them with commercially produced MHC or MHC-like proteins, then using these ex vivo complexes to bind to the target T cells. One should appreciated that the harvested T cells can included T cells that have been activated by the patient's immune response to the disease, exhausted T cells, or other T cells that are responsive to the discussed features.

EXAMPLES

The following description provides exemplary protocols to treat cancer in a patient according to the inventive subject matter. It should be understood that while these protocols list specific compounds and compositions alone or in combination, various alternative compounds and compositions may be provided with the same or similar effect. Moreover, dosage and schedules may change according to patient age, stage of cancer, and overall health condition.

Figure 3:
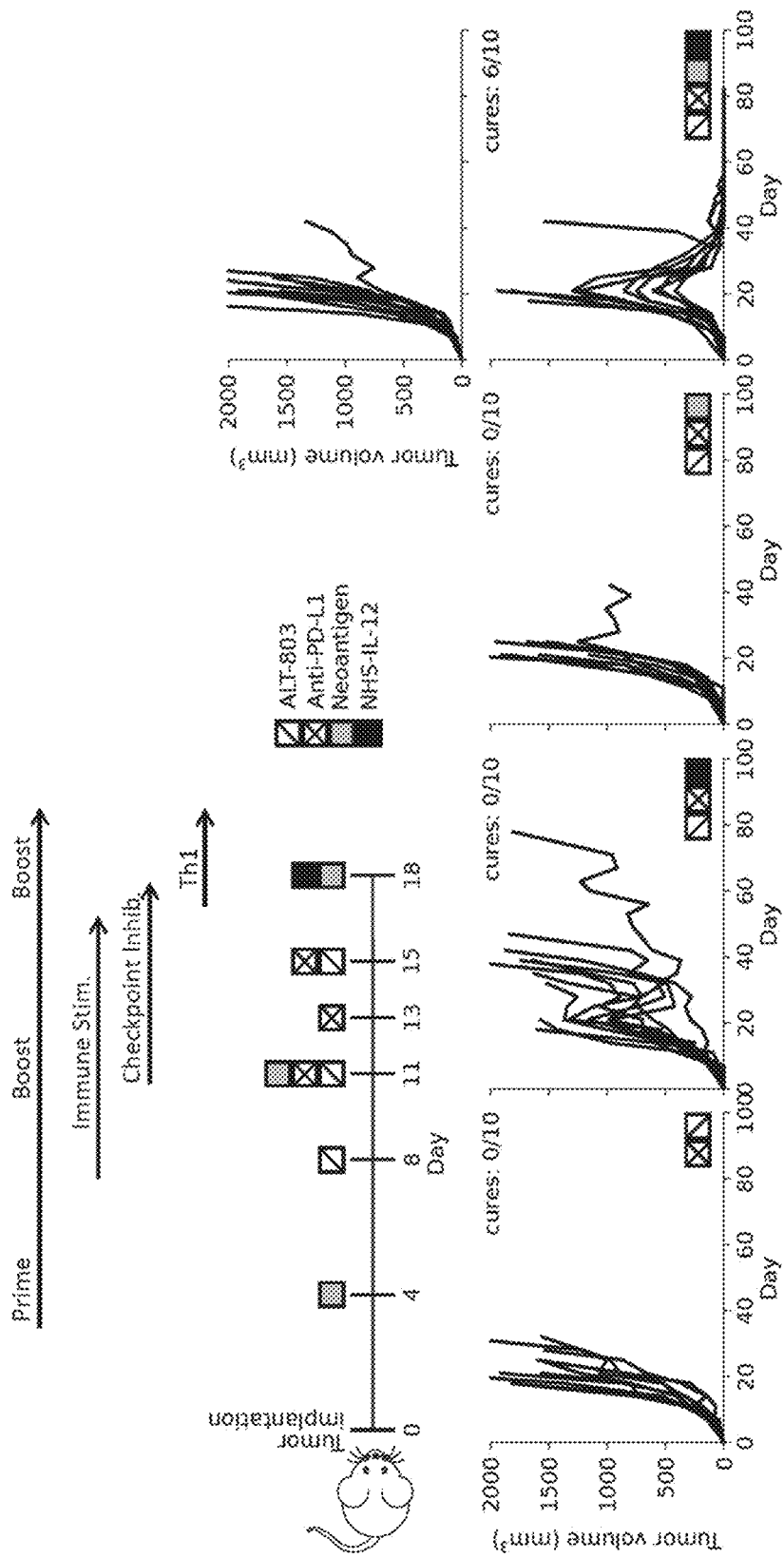
FIG. 3 is an exemplary schematic of various control experiments compared with a vaccination scheme according to the inventive subject matter.
Figure 4:
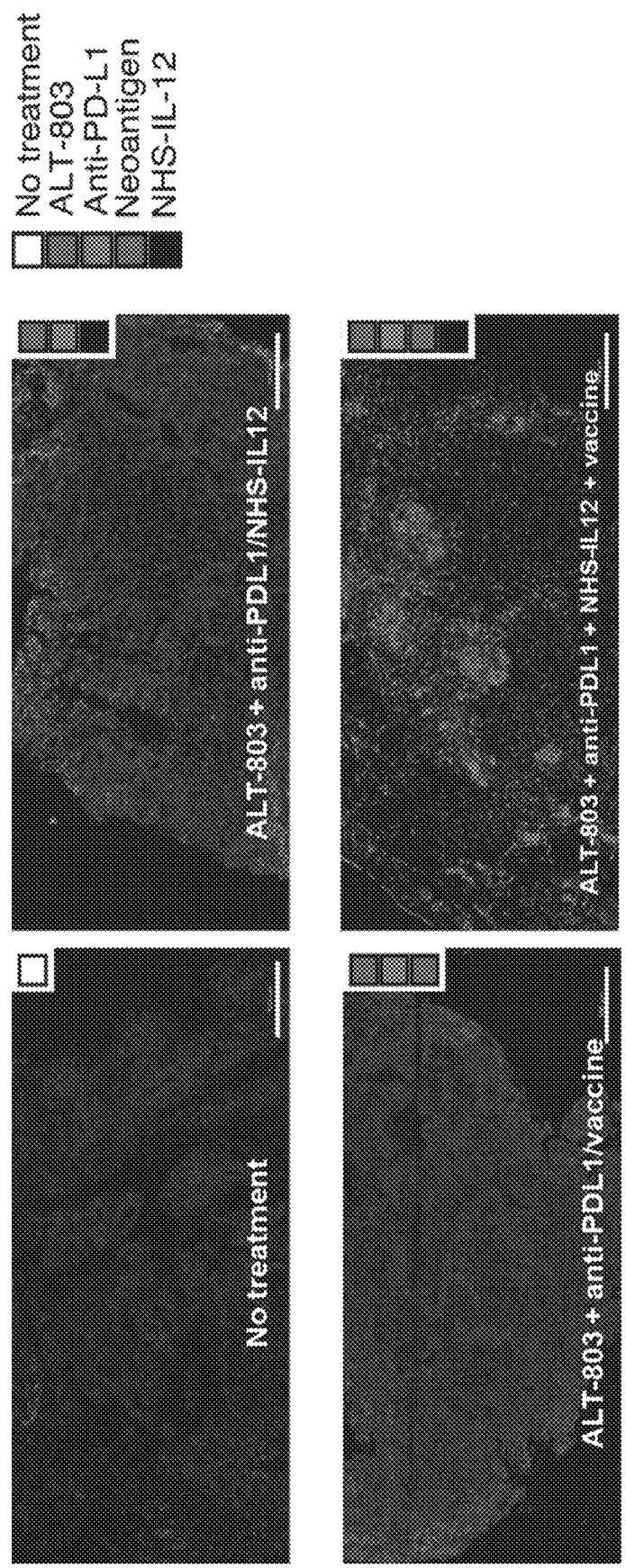
FIG. 4 depicts photomicrographs of CD8 T cell infiltration of tumors in animals of the schemes or FIG. 3.
Figure 5:
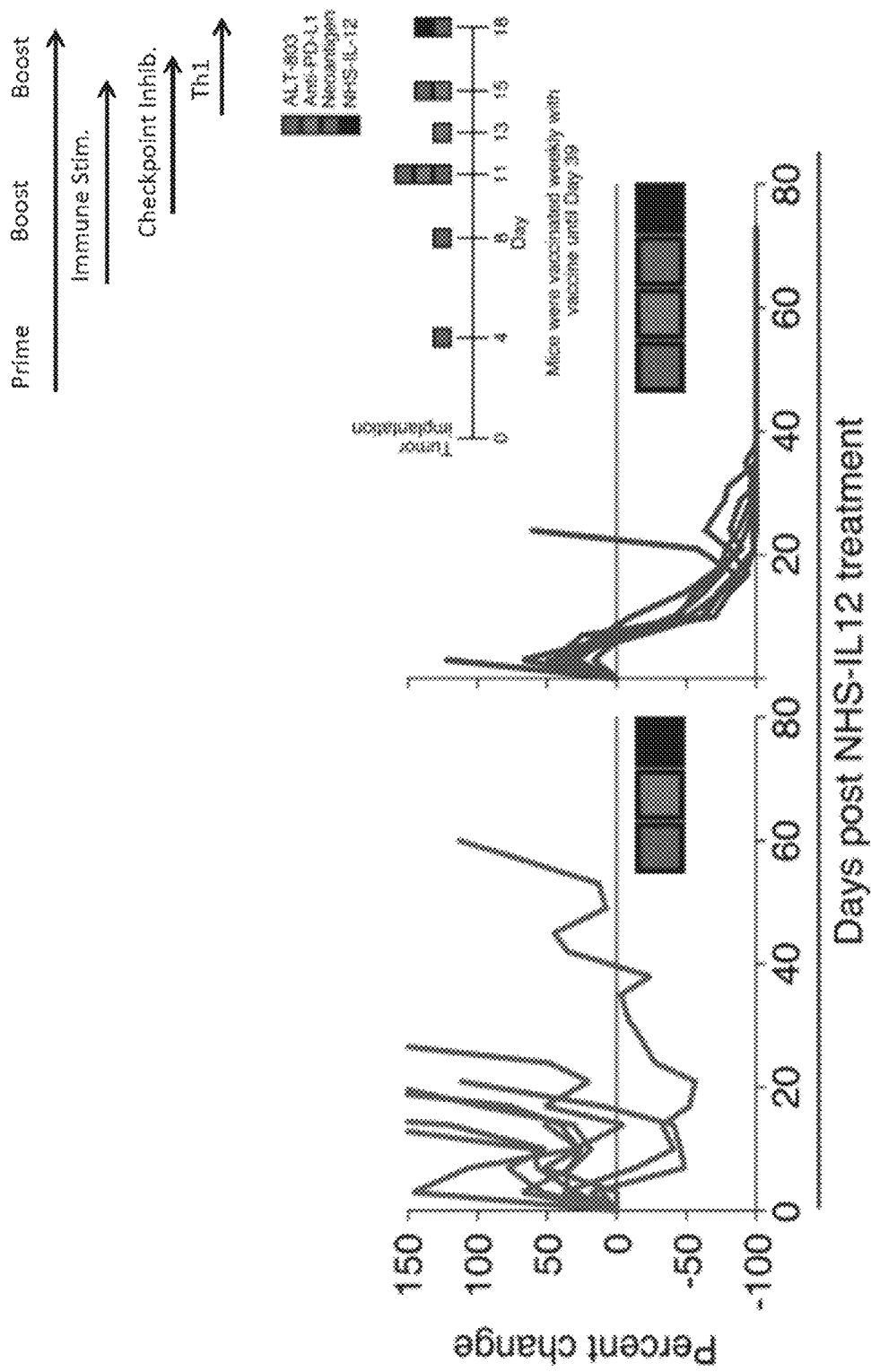
FIG. 5 is an exemplary graph of tumor volumes in animals treated using a scheme according to the inventive subject matter.

Example 1: As can be Readily Seen from FIG. 3, the Timed Sequence of Prime/Boost vaccination with immune stimulation and checkpoint inhibition and Th1 stimulation had dramatic effect (tumor volumes were significantly reduced after 40 days of combination treatment) as compared to any treatment regimen that lacked one of the components. This remarkable picture is also reflected in the histopathological analysis shown in FIG. 4. Here, photomicrographs are shown with CD8+ tumor infiltrating cells stained. Once more, the timed sequence of prime/boost vaccination with immune stimulation, checkpoint inhibition, and Th1 stimulation resulted in a significant increase in T cells infiltrating the tumor. FIG. 5 shows the results for a follow-up study indicating days after NHS IL-12 administration. Again, the effect of the timed sequence of prime/boost vaccination with immune stimulation and checkpoint inhibition and Th1 stimulation is readily apparent and resulted in all but two cured animals.

Example 2

Cell culture: MC38 and RMA-S cells were grown in RPMI-1640 with L-glutamine (Corning) supplemented with 10% (v/v) fetal bovine serum (Atlanta Biologicals) and 1% (v/v) antibiotic/antimitotic solution (Corning). All cells were cultured at 37° C., 5% CO2.

Animals and tumor implantation: Mice were handled in accordance with the Association for Assessment and Accreditation of Laboratory Animal Care guidelines, and under the approval of the NIH Intramural Animal Care and Use Committee. Mice were bred and housed at the NIH. Tumors were induced by implanting 3×105 tumor cells subcutaneously. All studies utilized female C57BL/6 animals.

Identification of tumor variants and neoepitopes: Single nucleotide variants (SNVs) and insertions/deletions (indels) were identified as previously described. Neoepitopes were identified by creating all possible permutations of 9-mer amino acid sequences derived from an identified non-silent SNV or indel. Neoepitopes were ranked by RNA expression as well as allele frequency of the observed coding variant to offset issues arising from tumor heterogeneity. NetMHC 3.4 was used to predict neoepitope binding to a specific MHC H-2 allele. Neoepitopes with predicted binding affinities<500 nM were retained for further analysis.

Peptide synthesis: Peptides were synthesized by Bio-Synthesis or GenScript to >85% purity.

Cell isolation and preparation: Spleens were harvested, dissociated through 70 μm filters and subjected to ACK lysis to obtain splenocytes for analysis. Tumors were harvested, cut into small pieces and incubated for 1 hour in a digestion cocktail comprised of RPMI supplemented with 5% (v/v) FBS, 2 mg/mL Collagenase Type I (Worthington Biochemical Corporation) and 40 U/mL DNase I (Calbiochem). Following digestion, tumors were ground through 70 μm filters and tumor-infiltrating leukocytes (TILs) were enriched using a 40%/70% Percoll (Sigma) gradient. Peripheral blood mononuclear cells (PBMCs) were isolated from whole, anti-coagulated mouse blood by layering over lymphocyte separation medium (MP Biomedicals) and collecting lymphocyte layer.

Flow cytometric assays: All antibodies used for flow cytometric analysis are fully described in Supplementary Table S1. Peptide binding assays were performed using RMA-S cells incubated with individual peptides at 50 μg/mL overnight. Following incubation, cells were stained with anti-MHC antibodies. Data were acquired using a flow cytometer, and reported as an in vitro binding score, which is the percentage of RMA-S cells expressing MHC on their surface. Tumor-infiltrating leukocytes were stained for immune cell subsets and data were collected using flow cytometer. Cell populations were identified as follows: CD8+T cells: live/CD45+/CD3+/CD8+; macrophages: live/CD45−/CD3−/CD11b+F4/80+. For intracellular cytokine staining, splenocytes were cultured with indicated peptides for 4 hours, at which time a protein transport inhibitor was added. Cultures were incubated an additional 20 hours, and fixed, permeabilized and stained for TNF and IFNγ production. Data were collected using an flow cytometer.

Vaccination and treatment with immune-modulators: Animals were vaccinated with pools of 9-mer or 25-mer neoepitope peptides (100 μg each peptide), emulsified, administered subcutaneously. Adenoviral vectors encoding TWIST1 or neoepitopes were kindly produced and provided by the Etubics/NantCell Corporation. 1010 viral particles encoding the multi-epitope virus were administered subcutaneously. The admixed virus was administered by injecting animals with 1010 viral particles each of which is a single-neoepitope encoding viruses subcutaneously. N-803 was kindly provided by Nantworks, and was administered subcutaneously into animals. Anti-PD-L1 (10F.9G2, BioXCell, 200 μg) was administered intraperitoneally. Murine NHS-IL12 was administered at a dose of 50 μg.

Assessment of immunity: Splenocytes or PBMCs were harvested and ex-vivo antigen-dependent cytokine secretion was assessed using IFNγ (BD Bioscience) or TNFα (Cellular Technology Ltd.) ELISPOT. Target peptides (10 μg/mL final concentration) were incubated with cells overnight. Assays were performed according to manufacturers' instructions. ELISPOT data are adjusted to the number of spots/million splenocytes after subtracting the number of spots in paired wells containing a control peptide.

Immunohistochemistry: Tumors, fixed in Z-fix (Anatech), were paraffin embedded and sectioned. Slides were stained for CD8a (4SM16). Images were acquired using an Axio Scan.Z1 slide scanner (Zeiss).

Depletion studies: Depletions were monitored in the peripheral blood via flow cytometry.

NanoString and T cell receptor (TCR) sequencing: Isolated tumor-infiltrating leukocytes were enriched using a CD45+ or CD4+/CD8+ murine TIL microbead kit (Miltenyi Biotech). RNA was purified from CD45+ cells using the RNeasy mini kit (Qiagen). Gene expression was assayed. Data was normalized using the nSolver Analysis Software 4.0. Genes whose expression was altered by at least 2-fold in biological replicates compared to non-treated control animals were considered to be significant. TCR diversity was assessed using genomic DNA purified from tumor-infiltrating CD4+ and CD8+ cells using the QIAamp DNA mini kit (Qiagen). TCRβ chain sequencing was performed by Adaptive Biotechnologies and analyzed using the Immunoseq analyzer. The top 100 TCR sequences were analyzed.

Data and statistical analysis: Flow cytometry data were analyzed using FlowJo (v10, BD Biosciences). All hierarchical clusters were generated using the Partek Genomics Suite. Statistics were performed using GraphPad Prism (v7; GraphPad Software). All data points represent the mean±SEM and P≤0.05 was considered significant. Significance is indicated within figures as follows: * P≤ 0.05,  P≤0.01, * P≤0.001, **** P≤0.0001.

Figure 6A:
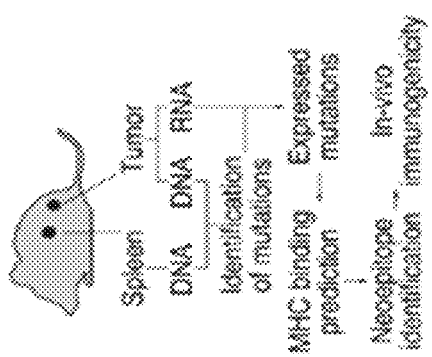
FIG. 6 show the procedures for identification of immunogenic neoepitopes. Panel 6A shows workflow for neoepitope discovery in subcutaneously implanted MC38 tumors. Panel 6B shows in-vitro binding score of MC38 neoepitopes. Panel 6C shows IFNγ ELISPOT analysis of naïve mice vaccinated twice with pools of 9-mer neoepitopes. Splenocytes were harvested 1 week following the second vaccination. Shaded bars represent peptides that induced robust immune responses in repeated experiments. Panel 6D shows treatment schedule. Panels 6E-F shows day 18 IFNγ ELISPOT analysis of mice vaccinated with (6E) four 9-mer or (6F) two 25-mer neoepitopes, alone or in combination with N-803 and/or anti-PD-L1. Panel 6G shows survival curves of tumor-bearing mice treated with N-803, anti-PD-L1 and four 9-mer neoepitope peptides (black line), N-803, anti-PD-L1 and PBS (dashed line), or no treatment (gray line). Panel 6H shows survival curves of mice treated with 9-mer neoepitope vaccine, N-803 and anti-PD-L1 stratified by antigen-specific IFNγ-secreting cells per 106 cells in the peripheral blood on day 13, *$P<0.05$.

Whole-exome DNA and RNA sequencing was performed on two MC38 tumors, and expressed nonsynonymous mutations were identified using a tumor-normal DNA analysis from splenocytes harvested from the same animals (FIG. 6A). Although both tumors were induced using MC38 cells harvested from the same culture flasks, the inventors observed a large difference in number of DNA mutations, and potential neoepitopes identified in each of the tumors analyzed (Table 1).

TABLE 1

|  | Tumor 1 | Tumor 2 |
| --- | --- | --- |
| Number of nonsynonymous mutations | 16828 | 8676 |
| Number of expressed nonsynonymous mutations | 7098 (42.2%) | 3548 (40.9%) |
| Number of nonsynonymous mutations predicted to bind MHC | 124 (0.7%) | 66 (0.8%) |
| Number of shared neoepitopes | 51 (0.3-0.5%) | |

Figure 6B:
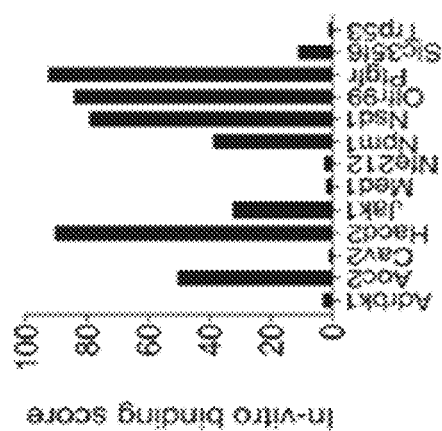
Figure 6C:
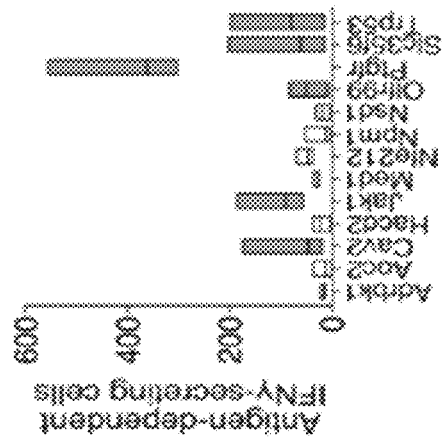
Figure 6F:
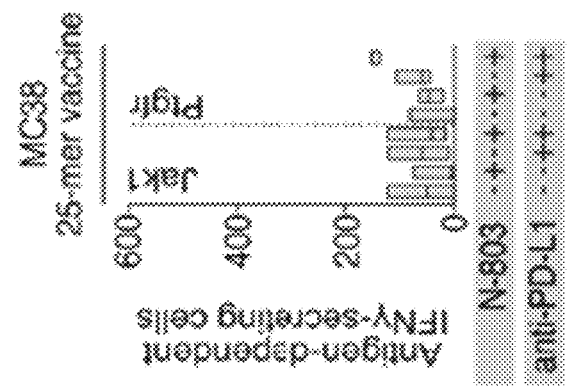
Figure 6E:
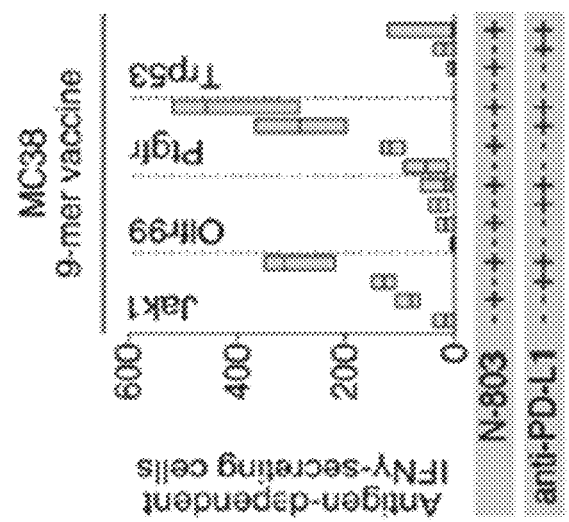
Figure 6D:
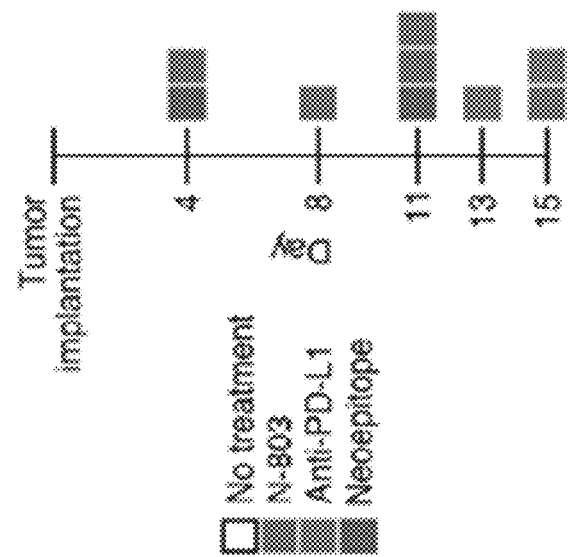
Figures 6G, 6H:
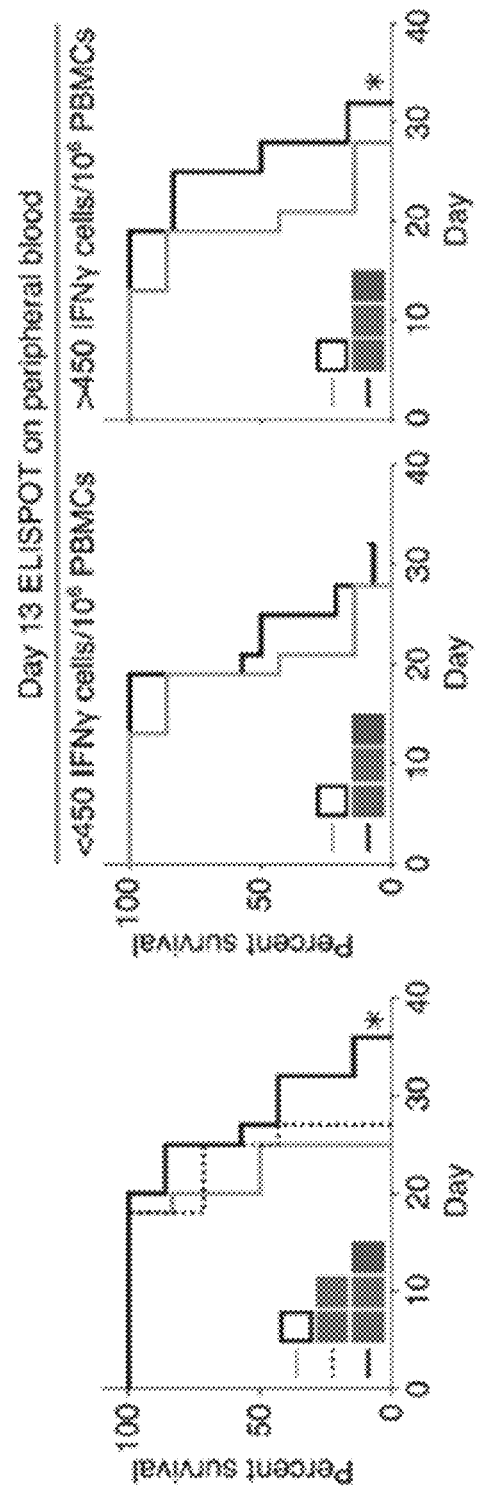

This observation is supportive of previous studies in which the MC38 tumor cell line has been identified as being microsatellite-unstable. In total, the inventors identified 51 potential neoepitopes, representing 43 unique nonsynonymous mutations, shared among both tumors assayed (Table 1). There continues to be no defined method of selecting appropriate nonsynonymous mutations to target with a vaccine; the inventors assumed that an ideal neoepitope would be both highly expressed and have a high affinity for binding MHC. Based upon this metric, the inventors initially ranked potential neoepitopes by dividing the relative expression by predicted MHC binding affinity. In addition, the inventors also utilized a second metric, which ranked neoepitopes solely by their predicted MHC binding affinity. Thirteen peptides, representing the top 10 peptides from both metrics were synthesized. Seven of these 13 neoepitopes were capable of binding MHC in-vitro (FIG. 6B), and the immunogenicity of each peptide was assessed by vaccinating non-tumor bearing mice with pools of emulsified neoepitope peptides. Using an ex-vivo IFNγ ELISPOT assay, 6/13 of the neoepitopes were found to induce immune responses in repeated experiments using non-tumor bearing animals (FIG. 6C, reactive peptides highlighted with shaded bars). Based upon these observations, we chose to utilize a vaccination strategy incorporating a pool of four 9-mer neoepitope peptides (Jak1, Olfr99, Ptgfr and Trp53). When administered as a single agent, the neoepitope vaccine induced a low level of immunity, but failed to provide any survival benefit as compared to control animals. In an effort to enhance the effectiveness of the neoepitope vaccine, the inventors combined it with the IL15 superagonist fusion protein N-803 and anti-PD-L1 MAb. Using the treatment regimen outlined in FIG. 6D, N-803 and anti-PD-L1 synergized to increase the immunogenicity of the 9-mer, but not 25-mer neoepitope vaccines in tumor bearing animals (FIGS. 6E and 6F). This enhancement in immunogenicity seen when combining our 9-mer neoepitope vaccine with N-803 and anti-PD-L1 correlated with only a slight, but significant increase in the survival of treated, as compared to control, animals (FIG. 6G). This survival benefit was seen only in animals mounting a robust immune response against vaccine components, as assessed by performing an ELIS-POT using peripheral blood collected from animals on day 13 of tumor growth (FIG. 6H).

Using the treatment regimen depicted in FIG. 7A, the inventors assayed the immune response in vaccinated animals on days 11, 18 and 25 of tumor growth, and observed that the magnitude of the immunity generated against vaccine components decreased over time. Interestingly, the inventors observed that the neoepitope vaccine also resulted in the in-situ expansion of T cells reactive against neoepitopes not contained in the vaccine. However, the magnitude of these de-novo immune responses also diminished over time despite continued vaccination (FIG. 7B). In an effort to promote the maintenance of neoepitope-reactive cells within the tumor microenvironment, the inventors incorporated a single injection of NHS-IL12 to the vaccine regimen on day 18 of tumor growth. Animals treated with the combination of anti-PD-L1, NHS-IL12, N-803 and neoepitope vaccine were able to maintain a robust immune response against neoepitopes Ptgfr and Trp53, both of which are components of the neoepitope vaccine, along with additional neoepitopes expressed by MC38 tumors, but not included in the vaccine (FIG. 7B). Interestingly, treatment of mice with N-803, anti-PD-L1 and NHS-IL12, but without vaccine, promoted only the expansion of T cells specific for a peptide (P15e) derived from GP70, an endogenous retrovirus protein expressed by MC38 cells, but not to any of the neoepitopes assayed (FIG. 7B).

Figures 7C, 7D:
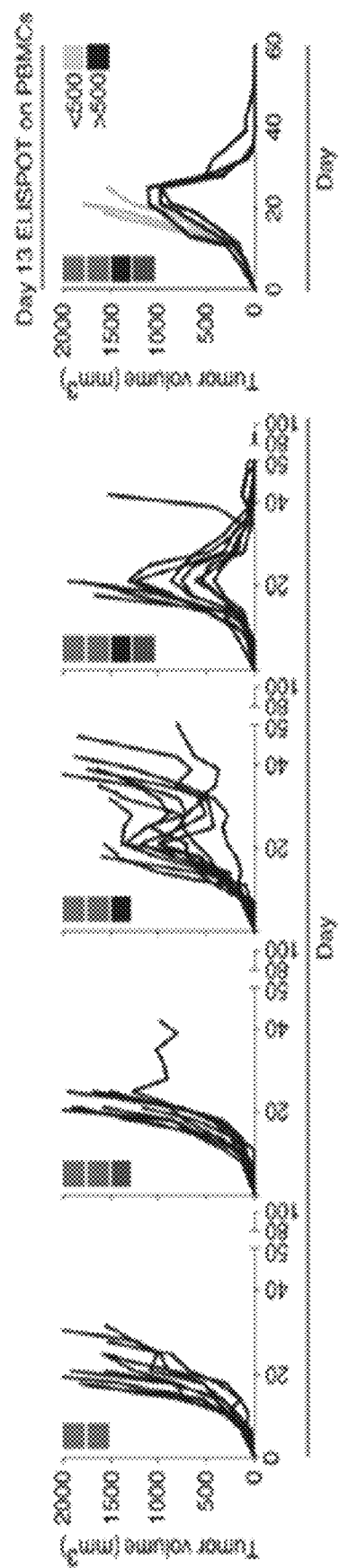
FIG. 7 show combination therapy using a 9-mer neoepitope vaccine, N-803, anti-PD-L1 and NHS-IL12. Panel 7A shows treatment schedule. Panel 7B shows IFNγ ELISPOT analysis on days 11, 18 and 25 of tumor growth against peptides contained within the vaccine (top) or MC38 neoepitopes not contained within the vaccine or P15e (bottom). Each column represents one mouse. Panel 7C shows tumor growth curves. Panel 7D shows tumor growth in mice treated with 9-mer neoepitope vaccine, N-803, anti-PD-L1 and NHS-IL12 stratified by antigen-specific IFNγ-secreting cells per 106 cells in the peripheral blood on day 13. Panel 7E shows survival curves after re-challenge of naïve animals or those with a previously regressed MC38 tumor following indicated treatment. Re-challenged animals were implanted with MC38 tumors on day 0 of survival curve and received no subsequent therapies. Arrow indicates depletion of CD8+ cells. Panel 7F-G show analysis of splenocytes from mice treated with 9-mer neoepitope vaccine, N-803, anti-PD-L1 and NHS-IL12, harvested on day 25 and stimulated overnight with either vaccine components or cascade antigens. Panel 7F shows ELISPOT analysis of the ratio of antigen-dependent TNFα:IFNγ secreting splenocytes. Panel 7G shows flow cytometric analysis of percent of CD8+ cells that were single IFNγ (orange), single TNFα (pink), or double (purple) producers. Panel 7H shows Tumor growth in mice treated with 9-mer neoepitope vaccine and NHS-IL12 according to the schedule in 7A.

In the presence or absence of vaccination, animals treated with N-803 and anti-PD-L1 showed no evidence of tumor control (FIG. 7C); in addition, animals treated with the combination of N-803, anti-PD-L1 and NHS-IL12, and no vaccine, had transient tumor control (FIG. 7C), with the median overall survival increasing from 21 days in non-treated animals to 39 days in animals treated with the triple combination. The addition of a neoepitope vaccine to this combination, however resulted in a dramatic regression of the majority of MC38 tumors (FIG. 7C, right panel). There was also a correlation as to which animals responded to this treatment via assessing the magnitude of the immune response generated against vaccine components as measured using peripheral blood collected from animals on day 13 of tumor growth, prior to the administration of NHS-IL12 (FIG. 7D). Animals whose tumors resolved following treatment remained tumor-free after the cessation of vaccination on day 39, and 4/6 animals subsequently resisted tumor re-challenge with MC38 on day 76. These re-challenged animals likely were able to completely clear any residual MC38 cells, as the inventors did not observe tumor outgrowth, even after depleting animals of CD8+ T cells 81 days after the second tumor implantation (FIG. 7E). Interestingly, the inventors observed a higher proportion of T cells producing TNFα in response to cascade neoepitopes as compared to those contained within the vaccine as assessed by ELISPOT (FIG. 7F). Similarly, flow cytometric analysis demonstrated a larger predominance of poly-functional T cells producing antigen-dependent IFNγ and TNFα in T cells reactive against cascade neoepitopes as compared to those contained within the vaccine (FIG. 7G). Animals treated with vaccine and NHS-IL12, using the same treatment timeline outlined in FIG. 7A, were able to mediate some degree of tumor regression in the absence of N-803 and anti-PD-L1 treatment; however, all of the treated animals eventually succumbed to progressive tumor growth. (FIG. 7H)

The dramatic regression of tumors in the combinatorial treatment group was associated with limited toxicity. All tissues examined were histologically normal with the exception of focal areas of glandular epithelial necrosis without inflammation in the duodenum, and hypercellularity in the small bowel of a treated animal. There was also a transient, slight increase in serum liver enzyme levels in treated mice that was not associated with any liver pathology.

Figure 8A:
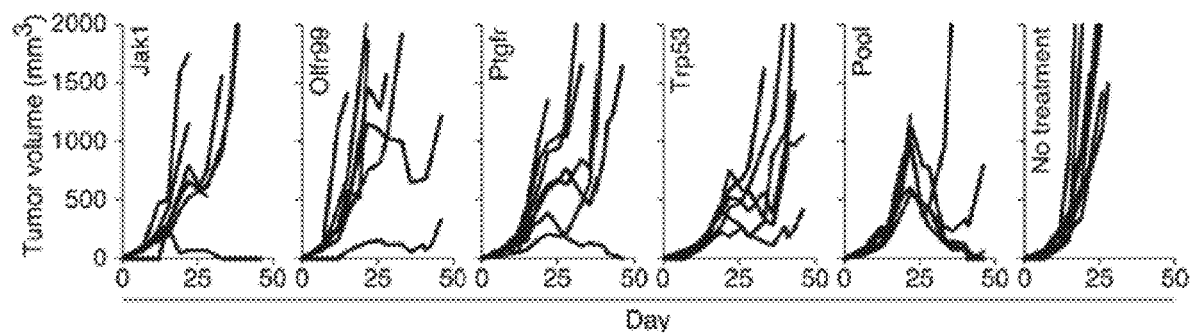
FIGS. 8 show tumor progression in mice treated with combination therapy using single-peptide vaccines or immune cell depletions. Panel 8A shows tumor growth in mice treated with N-803, anti-PD-L1, NHS-IL12 and a neoepitope vaccine consisting of a single 9-mer neoepitope or a pool of four 9-mer neoepitopes. Mice were treated according to the schedule in 7A. Panel 8B shows timeline (left) and tumor growth (right) of depletion studies. Tumor-bearing mice were depleted of NK, CD4 or CD8 cells starting 3 days prior to the first vaccine (early depletion) or NHS-IL12 administration (late depletion).
Figure 8B:
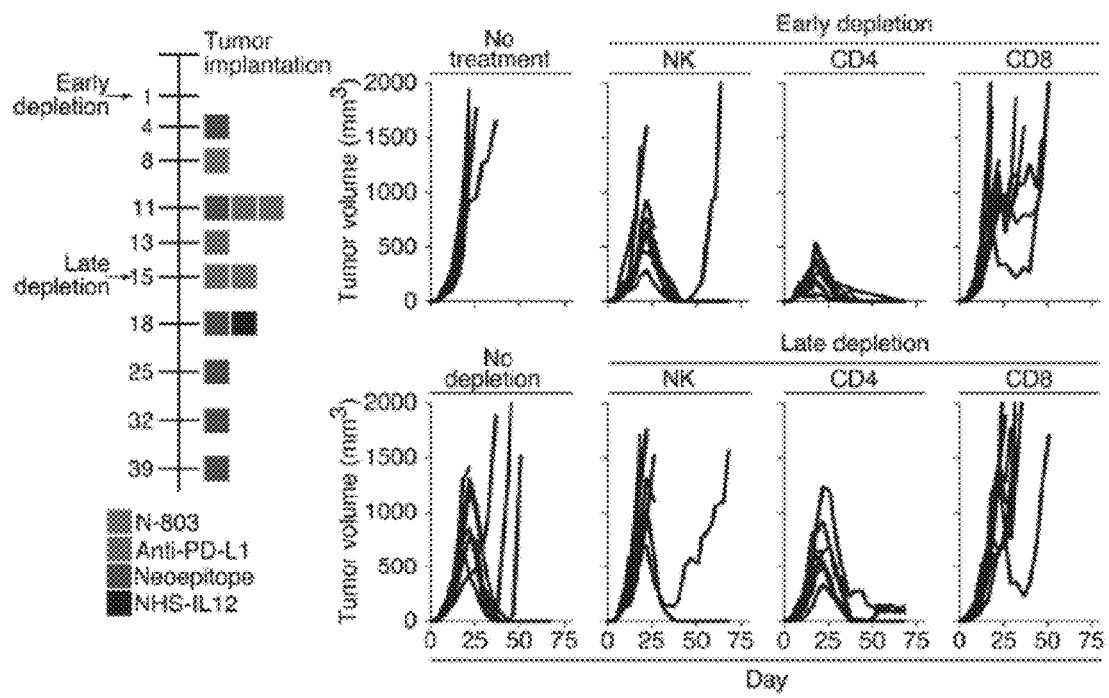

To ascertain if a vaccine consisting of a single neoepitope was capable of mediating tumor regression, tumor-bearing animals were treated with either a single 9-mer or a pool of all four neoepitope peptides in combination with N-803, anti-PD-L1 and NHS-IL12. The pool of neoepitopes was more efficient at inducing the regression of MC38 tumors than any of the single peptide vaccinations (FIG. 8A). To determine the cell populations mediating effective anti-tumor immunity, animals were depleted of NK1.1+, CD4+ or CD8+ T cells either beginning on day 1 of tumor growth (early depletion) or day 15 of tumor growth (late depletion). Animals depleted of NK1.1+ cells early during tumor growth were able to resolve MC38 tumors with kinetics similar to those seen in non-depleted animals. Early depletion of CD4+ cells in treated animals was associated with a more rapid regression of tumors as compared to non-depleted animals. Late depletion of NK1.1+ cells was associated with only 2/10 animals controlling tumor growth. Late depletion of CD4+ cells was associated with a rate of tumor resolution similar to that seen in non-depleted treated animals. As expected, both early and late depletion of CD8+ cells were associated with a lack of response to treatment, resulting in progressive tumor growth (FIG. 8B).

Figure 9A:
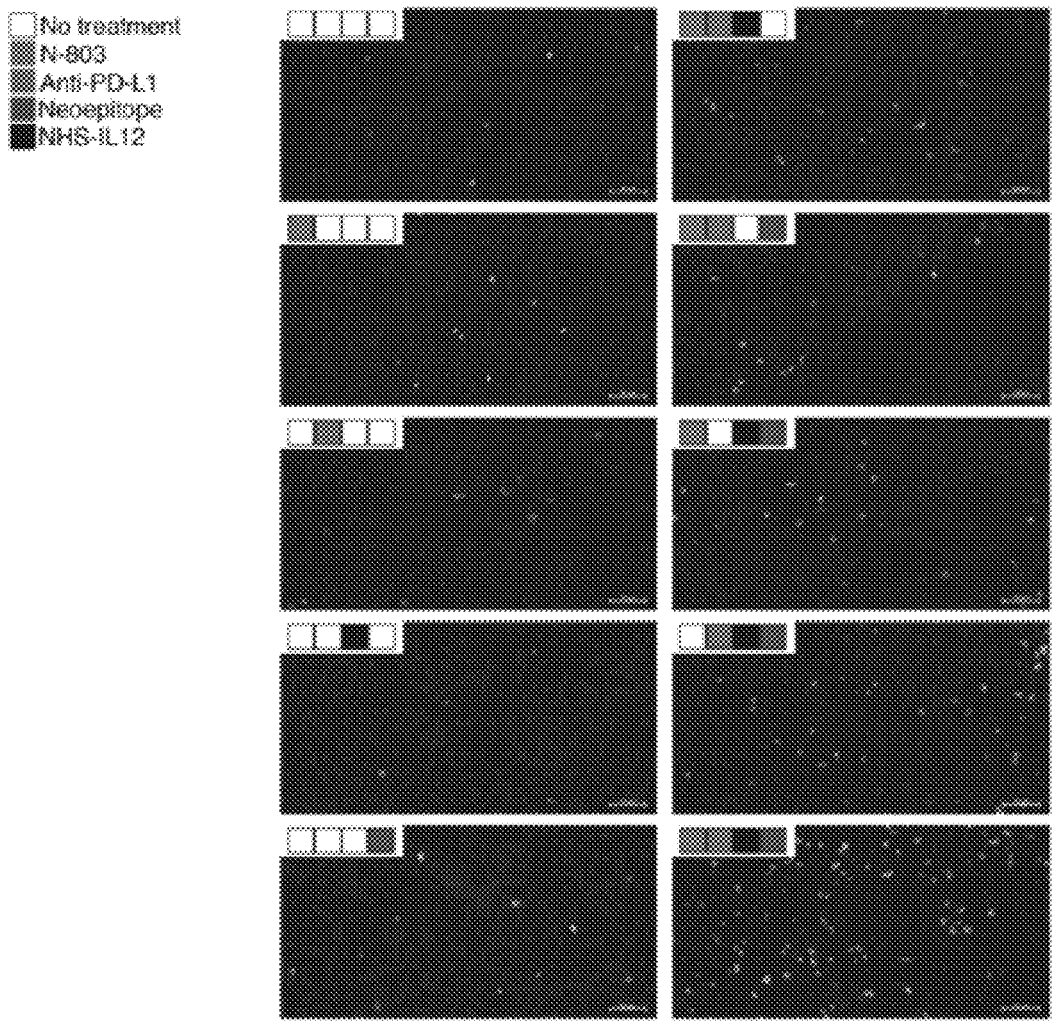
FIGS. 9 show tumor progression and tumor-infiltrating immune cells in mice treated with single, triple, or quadruple combinations of N-803, anti-PD-L1, NHS-IL12 and 9-mer neoepitope vaccine. Mice were treated as previously described, and tumors were harvested on day 22 post-tumor implantation. Tumors were analyzed via (9A+9B) immuno-fluorescent analysis or (9C+9D) flow cytometry. Panel 9A shows representative immunofluorescent images of CD8+ (red) cells in zinc formalin-fixed paraffin-embedded tumors sections. Blue corresponds to DAPI staining. Scale bar=50 μm. Panel 9B shows Percent CD8+ cells (of total DAPI+ cells) in immunofluorescent sections. Panel 9C shows intra-tumoral M1 macrophages (top,CD11b+F4/80+CD38+) and M2 macrophages (CD11b+F4/80+CD206+). Panel 9D shows CD8+ TIL maturation (CD44/CD62L/CD127). *$P<0.05$, $P<0.01$, *$P<0.001$, **** $P<0.0001$.
Figure 9B:
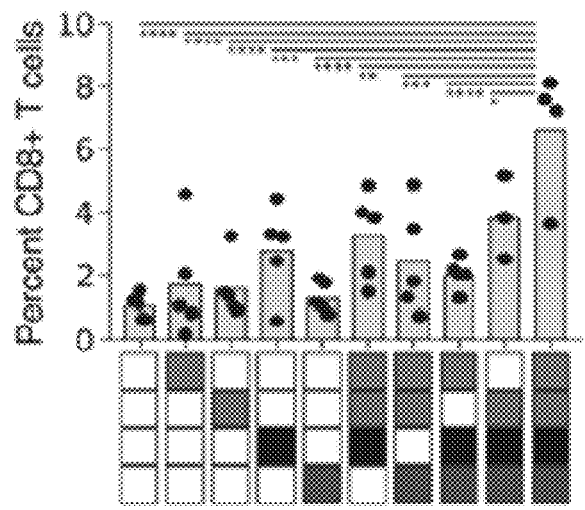
Figure 9C:
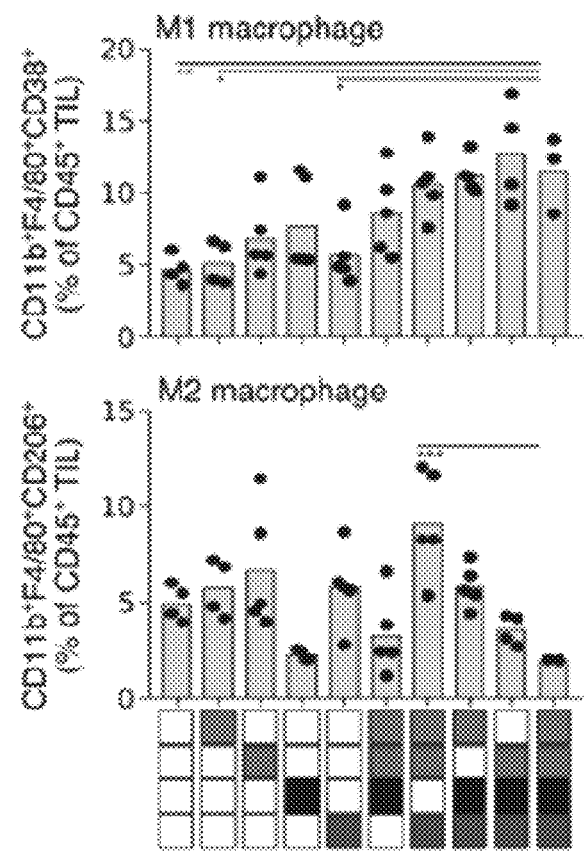
Figure 9D:
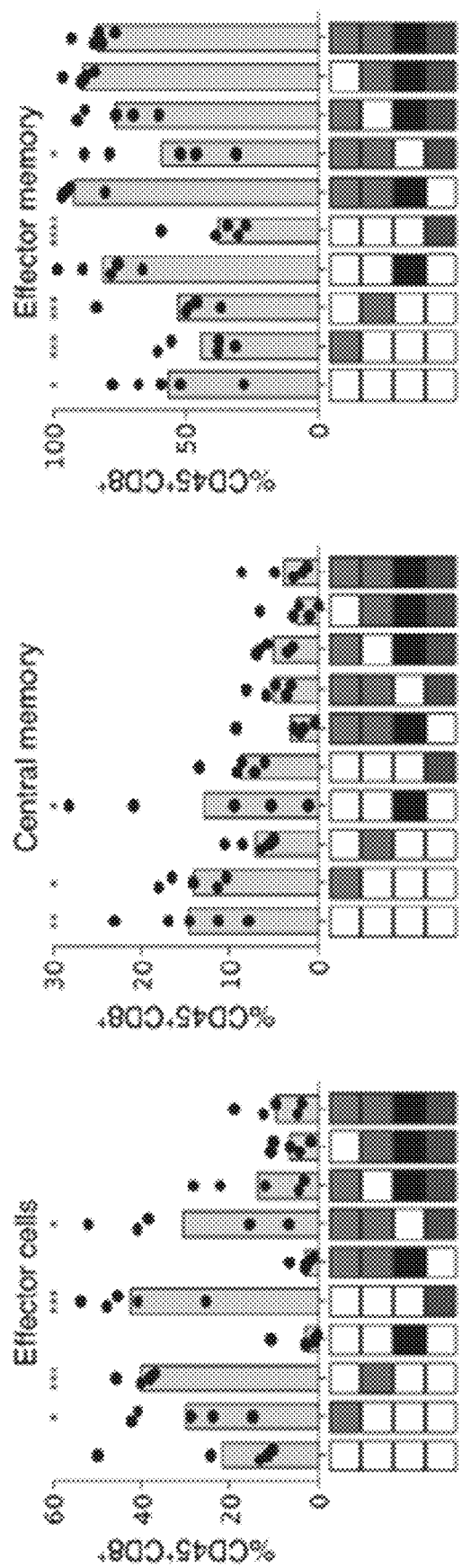

Using the same treatment regimen depicted in FIG. 7A, the inventors assessed which components of the immune system were modulated by each of the different agents and their combinations within the tumor microenvironment. The quadruple treatment regimen was shown to maximally enhance the infiltration of CD8+ T cells into the tumor (FIGS. 9A and 9B). The addition of NHS-IL12 to the treatment regimen had a profound impact on both the innate and adaptive immune cells within the tumor microenvironment. It promoted the expansion of M1 macrophages with a coordinate contraction of M2 macrophages (FIG. 9C); also observed was a trend in the reduction of effector and central memory CD8+ T cells, and an expansion of CD8+ effector memory cells (FIG. 9D). Treatment with vaccine and NHS-IL12 in combination with either N-803 or anti-PD-L1 was able to induce regression in 60% of MC38 tumors, as compared to 80% observed with the quad-therapy. Protective immunological memory was generated more efficiently in animals treated with either the quad-therapy or vaccine, anti-PD-L1 and NHS-IL12 as compared to animals treated with N-803, vaccine and NHS-IL12.

Figure 10A:
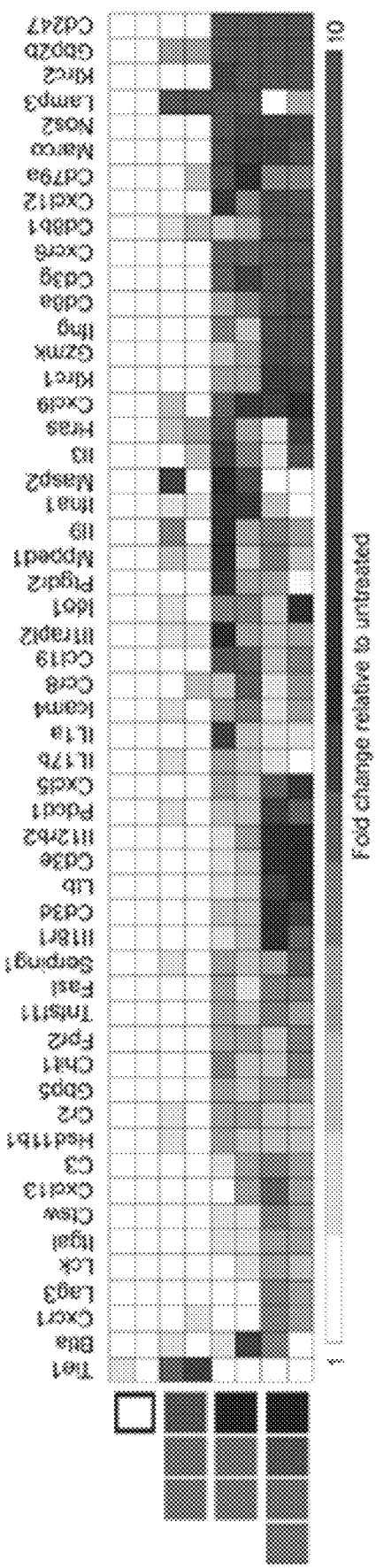
FIGS. 10 show Gene expression and clonality of tumor-infiltrating immune cells after treatment with a 9-mer neoepitope vaccine, N-803, anti-PD-L1 and NHS-IL12. Panel 10A shows gene expression analysis of tumor-infiltrating leukocytes. Panel 10B shows clonality of TCRβ chains detected in tumor infiltrates **$P<0.001$. Panel 10C shows number of TCRβ clones that comprise the top 25% of detected sequences. Panel 10D shows frequency of the top 100 TCRβ sequences detected in each sample. Each column represents one mouse, and each row represents a unique clone.

To better assess the impact of the treatment regimen on immune cells infiltrating the tumor, the inventors performed an analysis of gene expression in CD45+ cells isolated from day 25 tumors. Treatment of the combination of N-803, anti-PD-L1 and neoepitope vaccine had little observable impact on the expression of immune-related genes as compared to cells isolated from untreated tumors. The addition of NHS-IL12 to the N-803 and anti-PD-L1 treatment regimen correlated with an increased expression of a large number of genes primarily related to enhancement of the innate immune system. The addition of a neoepitope vaccine to this treatment, which was required to induce maximum tumor clearance, was associated with a great expansion of transcripts relating to T cell activation and effector functions (FIG. 10A).

Figures 10B, 10C, 10D:
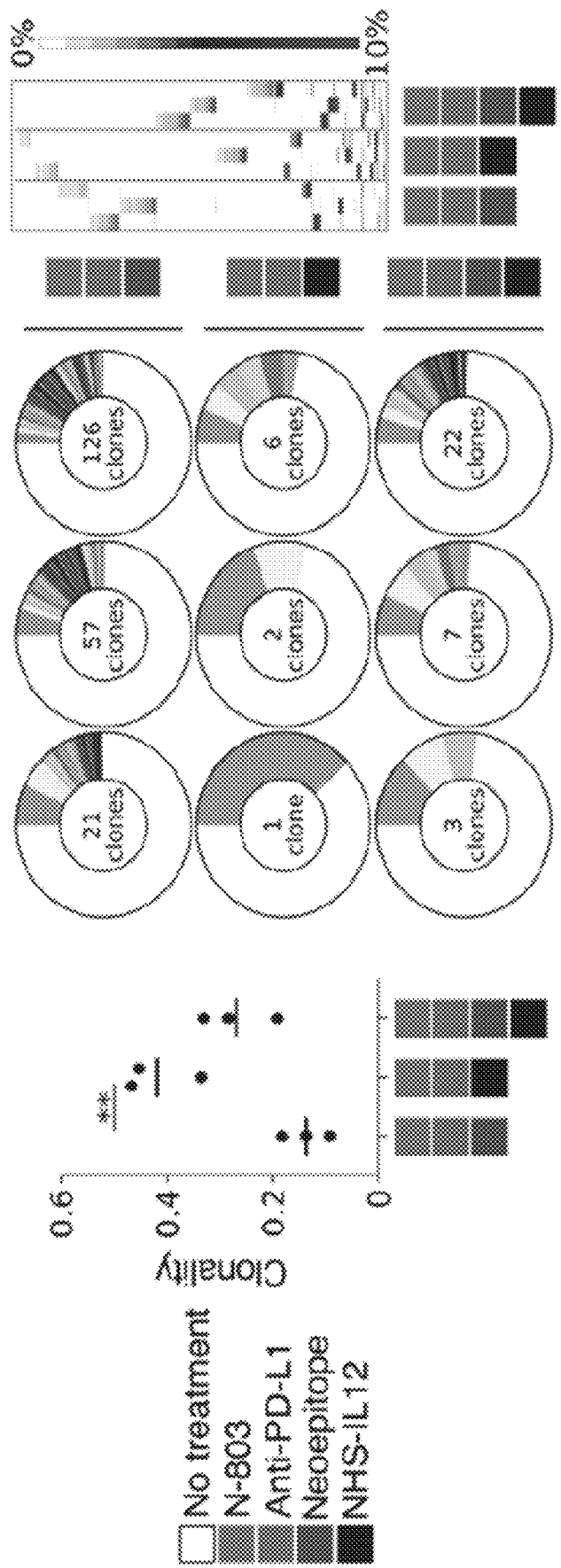

To assess the impact of the treatment on the diversity of the immune repertoire of cells infiltrating the tumor, the inventors sequenced the beta chain of the T cell receptor (TCRβ) of CD4+ and CD8+ cells isolated from day 25 tumors following treatment with indicated therapies. The use of NHS-IL12, N-803 and anti-PD-L1 in the treatment regimen resulted in the greatest increase in clonality of T cells within the tumor, which is modestly decreased upon incorporation of the neoepitope vaccine (FIG. 10B). To gain a better sense of the clonality of the T cell infiltrates within each tumor, the inventors examined the number of clones required to make up the top 25% of the productive clones. In mice treated with the neoepitope vaccine, N-803 and anti-PD-L1, the top 25% of productive rearrangements was composed of 21, 57 and 126 clones. The number decreased to 1, 2 and 6 in animals treated with N-803, anti-PD-L1 and NHS-IL12. With the addition of the neoepitope vaccine, which is required for tumor regression, the number of clones were 3, 7 and 22. These results indicate that NHS-IL12 drives the expansion of a limited number of clones, while the neoepitope vaccine broadens the repertoire, which associates with tumor clearance (FIG. 10C). An analysis of the top 100 TCRβ sequences detected in each sample revealed that each animal, regardless of treatment, had a unique T cell repertoire (FIG. 10D).

Figure 11A:
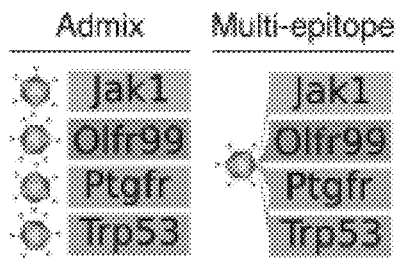
FIGS. 11 show combination therapy utilizing adenoviral vectors. Panel 11A shows Visual representation of admixed and multi-epitope adenoviral vaccines targeting neoepitopes. Panel 11B shows treatment schedule. Panel 11C shows IFNγ ELISPOT analysis on day 25 of tumor growth against neoepitopes contained within the vaccine. Each row represents one mouse. Panel 11D shows immune responses generated in animals vaccinated with multi-epitope adenovirus relative to paired neoepitopes from animals treated with admixed adenovirus. Each row represents one mouse. Panel 11E shows tumor growth curves. Panel 11F shows representative immunofluorescent images of CD8+(red) cells in zinc formalin-fixed, paraffin-embedded tumors sections. Blue corresponds to DAPI staining. Scale bar=50 μm. Panel 11G shows ratio of CD8:CD4 TIL in immunofluorescent sections. Panel 11H shows % FoxP3+ cells within immunofluorescent sections. Panel 11I shows tumor growth in mice treated as indicated in FIG. 11B utilizing an adenovirus targeting TWIST1. Panel 11J shows IFNγ ELISPOT analysis on day 25 of tumor growth against neoepitopes identified in the MC38 cell line. Each column represents one mouse. Panel 11K shows relative immunity of the immune responses generated in animals against neoepitopes in the adeno multi-epitope vaccinated animals as compared to animals vaccinated with adeno-TWIST1 vaccine. Each column represents one mouse.

Recombinant adenoviral vectors were produced that encoded either single neoepitopes or four neoepitopes in a single viral vector (FIG. 11A). Following the treatment schedule outlined in FIG. 11B, tumor-bearing animals were treated using an admix of four vectors with each single neoepitope vector administered at spatially separated injection sites, or a single viral vector encoding four neoepitopes (multi-epitope). Both the admix and multi-epitope vectors resulted in comparable immunity generated against the four neoepitopes comprising the vaccine (FIG. 11C); however, vaccination with the multi-epitope vector was more efficient at promoting the in-situ spread of immunity to neoepitopes expressed by the tumor, but not incorporated into the vector (FIG. 11D). The inventors hypothesized that one could facilitate epitope spread induced by the admixed vaccine by mixing the four preparations of viral particles prior to injection. However, even when all four admixed neoepitopes vaccines are administered together, and presumably activating T cells within the same draining lymph nodes, the admixed vaccine continues to be inefficient at mediating epitope spread as compared to the multi-epitope vaccine. This increased epitope spread observed with the administration of the multi-epitope vaccine associated with a more efficient tumor resolution in animals vaccinated with the multi-epitope vector, as compared to the admix of single neoepitope vectors (FIG. 11E). This protective anti-tumor immune response correlated with increased tumor infiltration of CD8+ T cells, along with a higher CD8:CD4 T cell ratio (FIGS. 11F and G). The inventors did not observe any differences in the presence of tumor-infiltrating T regulatory cells among the two experimental groups (FIG. 1111). Animals whose tumors resolved after treatment remained tumor-free even after the cessation of vaccination on day 39, and all animals subsequently resisted subsequent tumor re-challenge.

The inventors sought to determine if the degree of epitope spread detected on day 25 of tumor growth associated with a change in the rate of tumor growth in animals treated with the combination of neoepitope vaccine, N-803, anti-PD-L1 and NHS-IL12. The inventors observed a positive association between a decreased rate of tumor growth and the generation of epitope spread to numerous neoepitopes. Interestingly, there was no correlation of a decreased rate of tumor growth with the magnitude of immunity generated against the vaccine components or the P15e peptide.

Figure 11B:
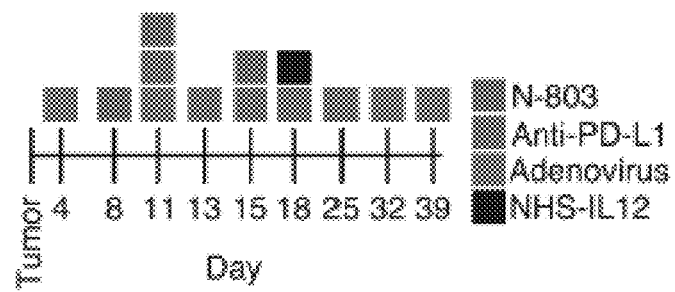
Figure 11C:
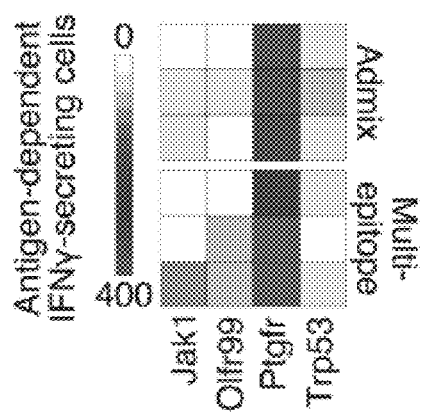
Figure 11D:
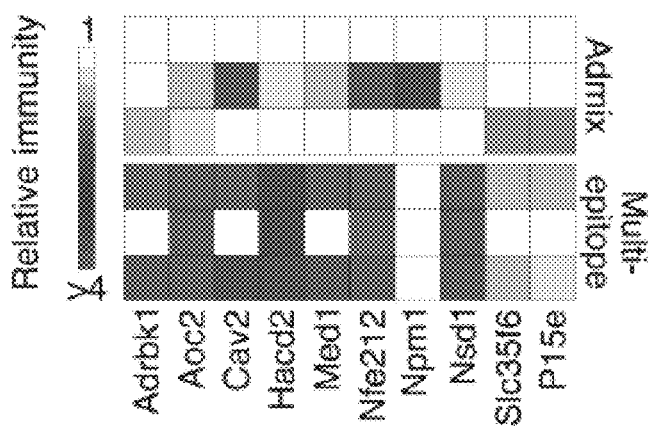
Figure 11E:
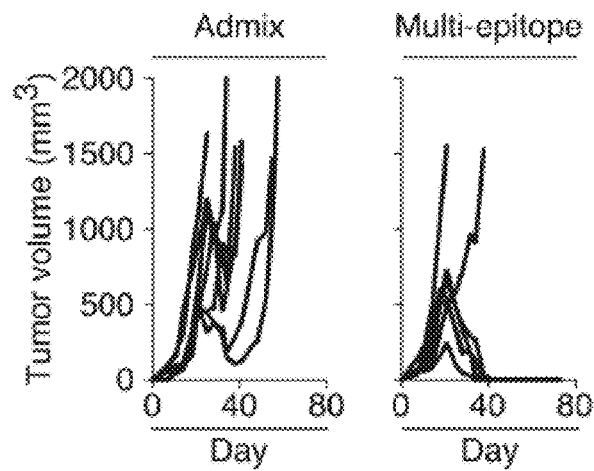
Figure 11F:
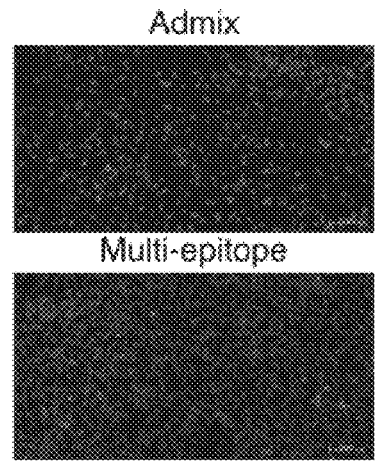
Figure 11G:
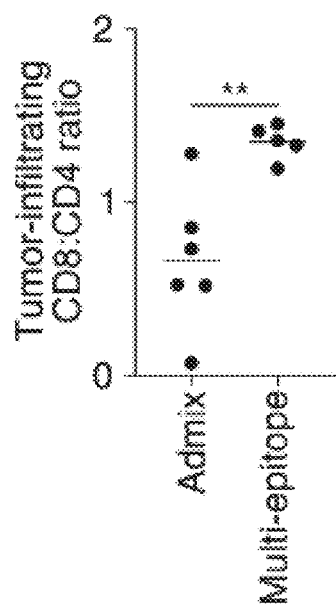
Figure 11H:
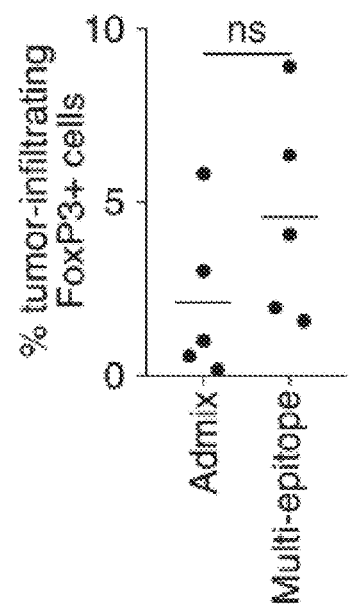
Figure 11I:
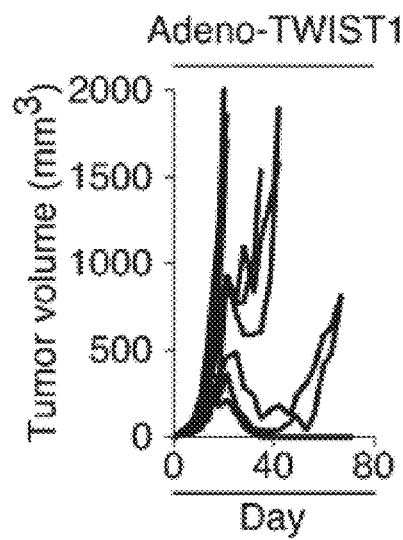
Figures 11J, 11K:
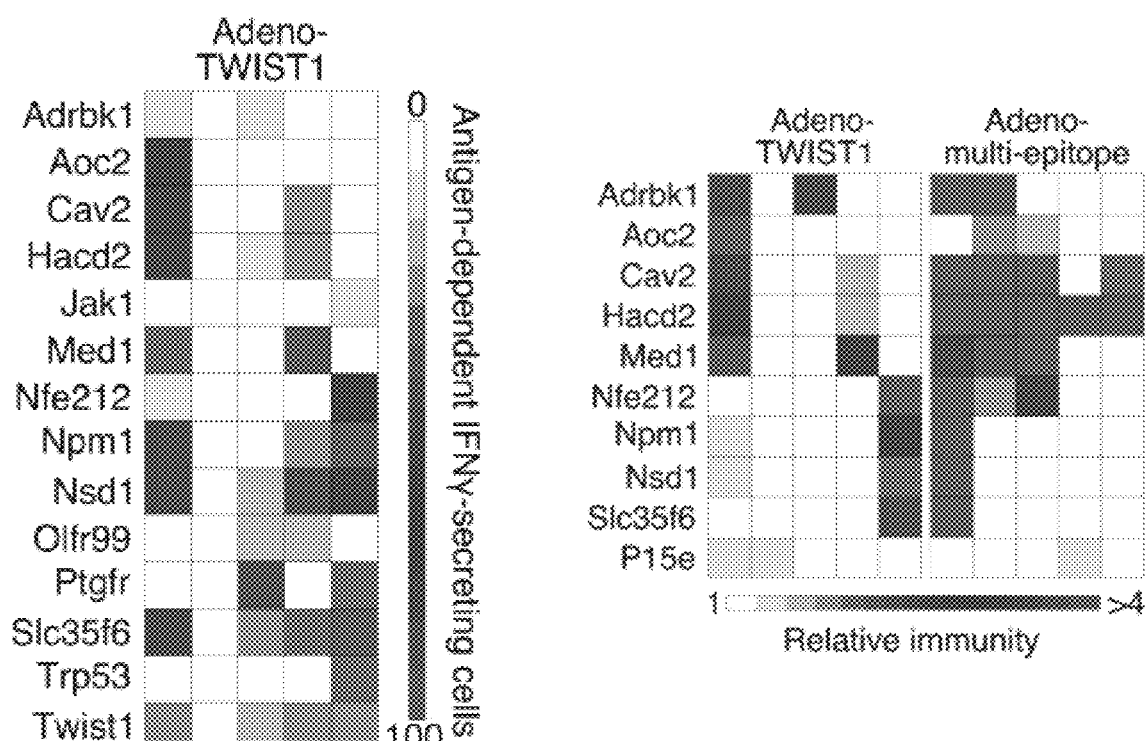

Utilizing the same treatment schedule and regimen including N-803, anti-PD-L1 and NETS-IL12 outlined in FIG. 11B, mice were vaccinated with an adenoviral vector encoding the 'self' tumor-associated antigen TWIST1, which is expressed by the MC38 cell line (32), and has been used in prior anti-cancer vaccine studies (33,34). Tumor regression was observed in only 2/10 animals treated with a regimen incorporating the TWIST1-targeted vaccine (FIG. 11I). Interestingly, TWIST1 vaccination was associated with the expansion of T cells reactive against tumor neoepitopes (FIG. 11J); however, the neoepitope vaccine is more efficient at mediating epitope spread than a vaccine targeting the tumor-associated antigen (FIG. 11K).

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. Unless the context dictates the contrary, all ranges set forth herein should be interpreted as being inclusive of their end points, and open-ended ranges should be interpreted to include commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Furthermore, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

As used herein, the term "treat", "treating" or "treatment" of any disease or disorder refers, in one embodiment, to the administration of one or more compounds or compositions for the purpose of ameliorating the disease or disorder (e.g., slowing or arresting or reducing the development of the disease or at least one of the clinical symptoms thereof). In another embodiment "treat", "treating", or "treatment" refers to the administration of one or more compounds or compositions for the purpose of alleviating or ameliorating at least one physical parameter including those which may not be discernible by the patient. In yet another embodiment, "treat", "treating", or "treatment" refers to the administration of one or more compounds or compositions for the purpose of modulating the disease or disorder, either symptomatically, (e.g., stabilization of a discernible symptom), physiologically, (e.g., breaking the escape phase of cancer immunoediting, induction of an elimination phase of cancer immunoediting, reinstatement of equilibrium phase of cancer immunoediting), or both. In yet another embodiment, "treat", "treating", or "treatment" refers to the administration of one or more compounds or compositions for the purpose of preventing or delaying the onset or development or progression of the disease or disorder. The terms "treat", "treating", and "treatment" may result, for example in the case of cancer in the stabilization of the disease, partial, or complete response. However, and especially where the cancer is treatment resistant, the terms "treat", "treating", and "treatment" do not imply a cure or even partial cure. As also used herein, the term "patient" refers to a human (including adults and children) or other mammal that is diagnosed or suspected to have a disease, and especially cancer.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of treating a tumor in an individual in need thereof, the method comprising:
    administering to the individual a first dose of a vaccine composition comprising at least four tumor neoepitope peptides or a nucleic acid encoding at least four tumor neoepitope peptides as a prime vaccination; wherein the tumor neoepitope peptides are determined by 1) whole genome sequencing of the individual's tumor and normal DNA, wherein 9-mer neoepitope peptides are identified as being encoded by the tumor DNA, 2) selecting from the neoepitope peptides those encoded by RNA with the greatest expression levels, and 3) selecting 9-mer neoepitope peptides for predicted binding affinity of <500nM for the HLA-type of the individual;
    administering to the individual Alt-803 after the prime vaccination;
    administering to the individual a PDL1 antibody after or concurrently with the Alt-803, wherein the PDL1 antibody is selected from the group consisting of 10F.9G2, atezolizumab, durvalumab, and avelumab;
    administering to the individual a second dose of the vaccine as a boost vaccination; and
    administering to the individual an effective amount of IL-12 after the boost vaccination.

2. The method of claim 1, wherein the prime vaccination and the boost vaccination are between 5 and 10 days apart.

3. The method of claim 1, wherein the administrations of Alt-803 and IL-12 are between 3-5 days apart.

4. The method of claim 1, wherein the nucleic acid encoding the tumor neoepitope peptides is in an expression vector selected from the group consisting of a bacterial expression vector, a yeast expression vector, and a viral expression vector.

5. The method of claim 4, wherein the nucleic acid vaccine composition comprises an adenoviral vector.

6. The method of claim 5, wherein the adenoviral vector encodes at least four neoepitope peptides.

* * * * *